United States Patent
Moretti et al.

(10) Patent No.: US 9,217,129 B2
(45) Date of Patent: Dec. 22, 2015

(54) OSCILLATING CELL CULTURE BIOREACTOR

(75) Inventors: Matteo G. Moretti, Milan (IT); Lisa E. Freed, Lexington, MA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1411 days.

(21) Appl. No.: 12/526,300

(22) PCT Filed: Feb. 8, 2008

(86) PCT No.: PCT/US2008/053411
§ 371 (c)(1),
(2), (4) Date: Aug. 11, 2010

(87) PCT Pub. No.: WO2008/098165
PCT Pub. Date: Aug. 14, 2008

(65) Prior Publication Data
US 2010/0297233 A1    Nov. 25, 2010

Related U.S. Application Data

(60) Provisional application No. 60/889,046, filed on Feb. 9, 2007.

(51) Int. Cl.
*C12M 3/00* (2006.01)
*C12M 1/00* (2006.01)
(Continued)

(52) U.S. Cl.
CPC ............... *C12M 23/02* (2013.01); *C12M 21/08* (2013.01); *C12M 23/06* (2013.01); *C12M 23/24* (2013.01); *C12M 25/14* (2013.01); *C12M 27/10* (2013.01); *A61L 27/3895* (2013.01)

(58) Field of Classification Search
CPC ...... C12M 21/08; C12M 23/02; C12M 23/06; C12M 23/24; C12M 25/14; C12M 27/10; A61L 27/3895
USPC ............. 435/284.1, 293.1; 623/916, 917, 921
See application file for complete search history.

(56) References Cited

U.S. PATENT DOCUMENTS 3,766,774 A * 10/1973 Clark .......................... 73/64.42
4,270,537 A    6/1981 Romaine
(Continued)

FOREIGN PATENT DOCUMENTS

| CA | 2453959 | 1/2003 |
| CA | 2649149 | 10/2007 |

(Continued)

OTHER PUBLICATIONS

Cerchia, et al. "Neutralizing aptamers from whole-cell SELEX inhibit the RET receptor tyrosine kinase", PLoS Biology, 3(4):849-60 (2005).

(Continued)

*Primary Examiner* — William H Beisner
(74) *Attorney, Agent, or Firm* — Pabst Patent Group LLP

(57) ABSTRACT

Methods and devices for cell or tissue culture are provided. One aspect provides a bioreactor having a gas permeable, closed-loop chamber for cell or tissue culture, and an oscillating means for moving the gas permeable, closed-loop chamber bidirectionally along an axis horizontal to an axis normal to the closed-loop chamber to force convection of cells and fluid in the gas permeable, closed-loop chamber. The bioreactor optionally includes a tissue engineering scaffold, an inlet means, an outlet means, and integrated sensors. Another aspect provides a bioreactor having a plurality of gas permeable, closed-loop chambers for cell or tissue culture. Methods of culturing cells and producing tissue constructs are also provided.

19 Claims, 5 Drawing Sheets

(51) Int. Cl.
  *C12M 1/12*  (2006.01)
  *C12M 1/04*  (2006.01)
  *C12M 3/04*  (2006.01)
  *A61L 27/38* (2006.01)

(56) References Cited

U.S. PATENT DOCUMENTS

| | | | |
|---|---|---|---|
| 4,446,122 A | 5/1984 | Chu et al. |
| 4,596,556 A | 6/1986 | Morrow et al. |
| 4,631,211 A | 12/1986 | Houghten |
| 4,638,045 A | 1/1987 | Kohn et al. |
| 4,790,824 A | 12/1988 | Morrow et al. |
| 4,795,436 A | 1/1989 | Robinson |
| 4,806,621 A | 2/1989 | Kohn et al. |
| 4,818,542 A | 4/1989 | DeLuca |
| 4,839,416 A | 6/1989 | Orenstein |
| 4,862,851 A | 9/1989 | Washino et al. |
| 4,886,499 A | 12/1989 | Cirelli et al. |
| 4,902,615 A | 2/1990 | Freeman et al. |
| 4,904,479 A | 2/1990 | Illum et al. |
| 4,940,460 A | 7/1990 | Casey et al. |
| 4,941,880 A | 7/1990 | Burns |
| 4,946,929 A | 8/1990 | D'Amore et al. |
| 4,959,219 A | 9/1990 | Chow et al. |
| RE33,405 E | 10/1990 | Chu et al. |
| 4,970,299 A | 11/1990 | Bazinet et al. |
| 4,976,968 A | 12/1990 | Steiner et al. |
| 5,010,167 A | 4/1991 | Ron et al. |
| 5,015,235 A | 5/1991 | Crossman |
| 5,019,379 A | 5/1991 | Domb et al. |
| 5,055,404 A | 10/1991 | Ueda et al. |
| 5,064,413 A | 11/1991 | McKinnon et al. |
| 5,069,936 A | 12/1991 | Yen |
| 5,093,246 A | 3/1992 | Cech et al. |
| 5,118,528 A | 6/1992 | Fessi et al. |
| 5,141,496 A | 8/1992 | Dalto et al. |
| 5,162,504 A | 11/1992 | Horoszewicz |
| 5,175,296 A | 12/1992 | Gerster |
| 5,190,521 A | 3/1993 | Hubbard et al. |
| 5,200,181 A | 4/1993 | Soltys |
| 5,240,963 A | 8/1993 | Domb |
| 5,270,163 A | 12/1993 | Gold et al. |
| 5,312,335 A | 5/1994 | McKinnon et al. |
| 5,328,483 A | 7/1994 | Jacoby |
| 5,334,144 A | 8/1994 | Alchas et al. |
| 5,334,497 A | 8/1994 | Inaba et al. |
| 5,339,163 A | 8/1994 | Homma et al. |
| 5,342,781 A | 8/1994 | Su |
| 5,383,851 A | 1/1995 | McKinnon, Jr. et al. |
| 5,389,640 A | 2/1995 | Gerster |
| 5,399,665 A | 3/1995 | Barrera et al. |
| 5,403,750 A | 4/1995 | Braatz et al. |
| 5,417,662 A | 5/1995 | Hjertman et al. |
| 5,449,513 A | 9/1995 | Yokoyama |
| 5,466,220 A | 11/1995 | Brenneman |
| 5,472,704 A | 12/1995 | Santus et al. |
| 5,480,381 A | 1/1996 | Weston |
| 5,500,161 A | 3/1996 | Andrianov et al. |
| 5,503,627 A | 4/1996 | McKinnon et al. |
| 5,512,600 A | 4/1996 | Mikos et al. |
| 5,514,378 A | 5/1996 | Mikos et al. |
| 5,520,639 A | 5/1996 | Peterson et al. |
| 5,527,288 A | 6/1996 | Gross et al. |
| 5,543,158 A | 8/1996 | Gref et al. |
| 5,567,588 A | 10/1996 | Gold et al. |
| 5,569,189 A | 10/1996 | Parsons |
| 5,578,325 A | 11/1996 | Domb et al. |
| 5,595,877 A | 1/1997 | Gold et al. |
| 5,599,302 A | 2/1997 | Lilley et al. |
| 5,649,912 A | 7/1997 | Peterson |
| 5,660,985 A | 8/1997 | Pieken et al. |
| 5,686,113 A | 11/1997 | Speaker |
| 5,696,175 A | 12/1997 | Mikos et al. |
| 5,696,249 A | 12/1997 | Gold et al. |
| 5,704,911 A | 1/1998 | Parsons |
| 5,716,404 A | 2/1998 | Vacanti et al. |
| 5,733,925 A | 3/1998 | Kunz et al. |
| 5,736,372 A | 4/1998 | Vacanti et al. |
| 5,744,155 A | 4/1998 | Friedman |
| 5,763,177 A | 6/1998 | Gold et al. |
| 5,766,635 A | 6/1998 | Spenleuhauer |
| 5,770,417 A | 6/1998 | Vacanti et al. |
| 5,786,204 A | 7/1998 | He et al. |
| 5,789,163 A | 8/1998 | Drolet et al. |
| 5,804,178 A | 9/1998 | Vacanti et al. |
| 5,817,785 A | 10/1998 | Gold et al. |
| 5,820,879 A | 10/1998 | Fernandez et al. |
| 5,837,752 A | 11/1998 | Shastri et al. |
| 5,843,653 A | 12/1998 | Gold et al. |
| 5,843,732 A | 12/1998 | Davis et al. |
| 5,853,984 A | 12/1998 | Davis et al. |
| 5,869,103 A | 2/1999 | Yah et al. |
| 5,871,747 A | 2/1999 | GengouxSedlik |
| 5,874,218 A | 2/1999 | Drolet et al. |
| 5,876,727 A | 3/1999 | Swain et al. |
| 5,879,712 A | 3/1999 | Bomberger et al. |
| 5,893,397 A | 4/1999 | Peterson et al. |
| 5,898,031 A | 4/1999 | Crooke |
| 5,902,599 A | 5/1999 | Anseth et al. |
| 5,916,539 A | 6/1999 | Pilgrimm |
| 5,928,647 A | 7/1999 | Rock |
| 5,942,252 A | 8/1999 | Tice |
| 5,958,691 A | 9/1999 | Pieken et al. |
| 5,977,089 A | 11/1999 | Arimilli et al. |
| 5,993,412 A | 11/1999 | Deily et al. |
| 6,001,577 A | 12/1999 | Gold et al. |
| 6,005,087 A | 12/1999 | Cook et al. |
| 6,007,845 A | 12/1999 | Domb et al. |
| 6,030,613 A | 2/2000 | Blumberg |
| 6,031,086 A | 2/2000 | Switzer |
| 6,039,969 A | 3/2000 | Tomai et al. |
| 6,043,224 A | 3/2000 | Lee et al. |
| 6,060,306 A * | 5/2000 | Flatt et al. ............ 435/297.2 |
| 6,083,505 A | 7/2000 | Miller et al. |
| 6,095,148 A | 8/2000 | Shastri et al. |
| 6,107,094 A | 8/2000 | Crooke |
| 6,110,462 A | 8/2000 | Barbas et al. |
| 6,120,666 A | 9/2000 | Jacobson |
| 6,123,727 A | 9/2000 | Vacanti et al. |
| 6,127,533 A | 10/2000 | Cook et al. |
| 6,184,364 B1 | 2/2001 | Pieken et al. |
| 6,190,913 B1 | 2/2001 | Singh |
| 6,197,346 B1 | 3/2001 | Mathiowitz et al. |
| 6,225,460 B1 | 5/2001 | Bischofberger et al. |
| 6,232,082 B1 | 5/2001 | Ennifar et al. |
| 6,235,313 B1 | 5/2001 | Mathiowitz et al. |
| 6,238,705 B1 | 5/2001 | Liu et al. |
| 6,242,246 B1 | 6/2001 | Gold et al. |
| 6,245,776 B1 | 6/2001 | Skwierczynski |
| 6,254,890 B1 | 7/2001 | Hirosue et al. |
| 6,265,608 B1 | 7/2001 | Summer, Jr. |
| 6,288,040 B1 | 9/2001 | Muller et al. |
| 6,344,318 B1 | 2/2002 | Gold et al. |
| 6,348,462 B1 | 2/2002 | Gerster et al. |
| 6,365,187 B2 | 4/2002 | Mathiowitz et al. |
| 6,376,190 B1 | 4/2002 | Gold et al. |
| 6,395,718 B1 | 5/2002 | Alusher et al. |
| 6,399,754 B1 | 6/2002 | Cook |
| 6,403,779 B1 | 6/2002 | Kawasaki et al. |
| 6,429,200 B1 | 8/2002 | Monahan et al. |
| 6,451,527 B1 | 9/2002 | Larocca et al. |
| 6,458,539 B1 | 10/2002 | Gold et al. |
| 6,458,543 B1 | 10/2002 | Gold et al. |
| 6,482,594 B2 | 11/2002 | Gold et al. |
| 6,492,554 B2 | 12/2002 | Dalton et al. |
| 6,506,559 B1 | 1/2003 | Fire et al. |
| 6,506,577 B1 | 1/2003 | Deming et al. |
| 6,528,499 B1 | 3/2003 | Kozikowski |
| 6,558,951 B1 | 5/2003 | Tomai et al. |
| 6,569,896 B2 | 5/2003 | Dalton et al. |
| 6,589,562 B1 | 7/2003 | Shefer et al. |
| 6,589,563 B2 | 7/2003 | Prokop et al. |
| 6,608,201 B2 | 8/2003 | Gerster et al. |
| 6,610,319 B2 | 8/2003 | Tomai et al. |

(56) References Cited

U.S. PATENT DOCUMENTS

| | | |
|---|---|---|
| 6,610,713 B2 | 8/2003 | Tracey et al. |
| 6,632,922 B1 | 10/2003 | Deming et al. |
| 6,656,469 B1 | 12/2003 | Svensson |
| 6,686,446 B2 | 2/2004 | Deming et al. |
| 6,686,472 B2 | 2/2004 | Gerster et al. |
| 6,696,076 B2 | 2/2004 | Tomai et al. |
| 6,699,474 B1 | 3/2004 | Cerny et al. |
| 6,716,583 B2 | 4/2004 | Gold et al. |
| 6,723,429 B2 | 4/2004 | Bengs et al. |
| 6,737,056 B1 | 5/2004 | Presta |
| 6,767,702 B2 | 7/2004 | Mirkin |
| 6,818,732 B2 | 11/2004 | Deming et al. |
| 6,838,484 B2 | 1/2005 | Steiner et al. |
| 6,875,605 B1 | 4/2005 | Ma |
| 6,875,886 B2 | 4/2005 | Frangioni |
| 6,902,743 B1 | 6/2005 | Setterstrom |
| 6,932,971 B2 | 8/2005 | Bachmann et al. |
| 6,995,284 B2 | 2/2006 | Dalton et al. |
| 6,998,500 B2 | 2/2006 | Dalton et al. |
| 7,008,411 B1 | 3/2006 | Mandrusov et al. |
| 7,022,870 B2 | 4/2006 | Dalton et al. |
| 7,026,500 B2 | 4/2006 | Dalton et al. |
| 7,029,859 B2 | 4/2006 | Thompson |
| 7,030,228 B1 | 4/2006 | Schmitz et al. |
| 7,056,704 B2 | 6/2006 | Tuschl et al. |
| 7,078,196 B2 | 7/2006 | Tuschl et al. |
| 7,097,837 B2 | 8/2006 | Nielsen et al. |
| 7,149,574 B2 | 12/2006 | Yun |
| 7,163,680 B2 | 1/2007 | Bander |
| 7,247,502 B2 | 7/2007 | Ennifar et al. |
| 7,250,499 B2 | 7/2007 | Mirkin et al. |
| 7,335,744 B2 | 2/2008 | Liu |
| 7,363,076 B2 | 4/2008 | Yun |
| 7,375,180 B2 | 5/2008 | Gorden et al. |
| 7,387,271 B2 | 6/2008 | Noelle |
| 7,422,902 B1 | 9/2008 | Wheeler et al. |
| 7,427,629 B2 | 9/2008 | Kedl et al. |
| 7,488,792 B2 | 2/2009 | Ruoslahti |
| 7,550,441 B2 | 6/2009 | Farokhzad et al. |
| 7,727,969 B2 | 6/2010 | Farokhzad |
| 7,762,803 B2 | 7/2010 | Nakazato |
| 7,767,803 B2 | 8/2010 | Diener |
| 2001/0012890 A1 | 8/2001 | Thompson |
| 2002/0009466 A1 | 1/2002 | Brayden |
| 2002/0064780 A1 | 5/2002 | Gold et al. |
| 2002/0068091 A1 | 6/2002 | Davis et al. |
| 2002/0086356 A1 | 7/2002 | Tuschl et al. |
| 2002/0099036 A1 | 7/2002 | Dalton et al. |
| 2002/0099096 A1 | 7/2002 | Dalton et al. |
| 2002/0102613 A1 | 8/2002 | Hogenboom |
| 2002/0106647 A1 | 8/2002 | Segal |
| 2002/0116054 A1* | 8/2002 | Lundell et al. .................. 623/2.1 |
| 2002/0119916 A1 | 8/2002 | Hassan |
| 2002/0150578 A1 | 10/2002 | He et al. |
| 2002/0151004 A1 | 10/2002 | Craig |
| 2002/0153251 A1 | 10/2002 | Sassi et al. |
| 2002/0156125 A1 | 10/2002 | Broder et al. |
| 2002/0173495 A1 | 11/2002 | Dalton et al. |
| 2003/0003103 A1 | 1/2003 | Thompson |
| 2003/0009029 A1 | 1/2003 | Buchholz et al. |
| 2003/0022868 A1 | 1/2003 | Dalton et al. |
| 2003/0035804 A1 | 2/2003 | D'Amico et al. |
| 2003/0054360 A1 | 3/2003 | Gold et al. |
| 2003/0087301 A1 | 5/2003 | Smith et al. |
| 2003/0099668 A1 | 5/2003 | Bachmann |
| 2003/0108611 A1 | 6/2003 | Bosch et al. |
| 2003/0108923 A1 | 6/2003 | Tuschl et al. |
| 2003/0133988 A1 | 7/2003 | Fearon et al. |
| 2003/0134810 A1 | 7/2003 | Springate et al. |
| 2003/0138557 A1 | 7/2003 | Allison |
| 2003/0143184 A1 | 7/2003 | Seo et al. |
| 2003/0162761 A1 | 8/2003 | Steiner et al. |
| 2003/0165478 A1 | 9/2003 | Sokoll et al. |
| 2003/0175950 A1 | 9/2003 | McSwiggen |
| 2003/0219766 A1 | 11/2003 | Raitano et al. |
| 2003/0225040 A1 | 12/2003 | Dalton et al. |
| 2003/0232013 A1 | 12/2003 | Sieckman et al. |
| 2003/0232792 A1 | 12/2003 | Dalton et al. |
| 2003/0235619 A1 | 12/2003 | Allen |
| 2004/0014789 A1 | 1/2004 | Lau et al. |
| 2004/0014975 A1 | 1/2004 | Dalton et al. |
| 2004/0022727 A1 | 2/2004 | Stanton |
| 2004/0022840 A1 | 2/2004 | Nagy et al. |
| 2004/0029913 A1 | 2/2004 | Dalton et al. |
| 2004/0043923 A1 | 3/2004 | Parma et al. |
| 2004/0052727 A1 | 3/2004 | Dalton et al. |
| 2004/0054190 A1 | 3/2004 | Pomper |
| 2004/0059094 A1 | 3/2004 | Bachmann et al. |
| 2004/0067196 A1 | 4/2004 | Brunke et al. |
| 2004/0067503 A1 | 4/2004 | Tan et al. |
| 2004/0067979 A1 | 4/2004 | Dalton et al. |
| 2004/0072234 A1 | 4/2004 | Parma et al. |
| 2004/0086544 A1 | 5/2004 | Bezemer et al. |
| 2004/0087810 A1 | 5/2004 | Dalton et al. |
| 2004/0092470 A1 | 5/2004 | Leonard et al. |
| 2004/0136961 A1 | 7/2004 | Prokop et al. |
| 2004/0141958 A1 | 7/2004 | Steinaa |
| 2004/0147489 A1 | 7/2004 | Dalton et al. |
| 2004/0147550 A1 | 7/2004 | Dalton et al. |
| 2004/0156846 A1 | 8/2004 | Daum et al. |
| 2004/0167103 A1 | 8/2004 | Dalton et al. |
| 2004/0192626 A1 | 9/2004 | McSwiggen et al. |
| 2004/0241790 A1 | 12/2004 | Eriksen et al. |
| 2004/0247680 A1 | 12/2004 | Farokhzad et al. |
| 2004/0248088 A1 | 12/2004 | Raitano et al. |
| 2004/0260092 A1 | 12/2004 | Miller et al. |
| 2004/0260108 A1 | 12/2004 | Dalton et al. |
| 2004/0266688 A1 | 12/2004 | Nayak et al. |
| 2005/0017667 A1 | 1/2005 | Yamamoto |
| 2005/0019870 A1 | 1/2005 | Afar et al. |
| 2005/0019872 A1 | 1/2005 | Afar et al. |
| 2005/0020525 A1 | 1/2005 | McSwiggen et al. |
| 2005/0032733 A1 | 2/2005 | McSwiggen et al. |
| 2005/0033074 A1 | 2/2005 | Dalton et al. |
| 2005/0037075 A1 | 2/2005 | Farokhzad et al. |
| 2005/0048063 A1 | 3/2005 | Ruoslahti et al. |
| 2005/0069910 A1 | 3/2005 | Turner et al. |
| 2005/0079152 A1 | 4/2005 | Bot et al. |
| 2005/0079533 A1 | 4/2005 | Samuelson et al. |
| 2005/0079553 A1 | 4/2005 | Ayyoub et al. |
| 2005/0080128 A1 | 4/2005 | Tsukamoto et al. |
| 2005/0100877 A1 | 5/2005 | Xu et al. |
| 2005/0107322 A1 | 5/2005 | OHagan et al. |
| 2005/0122550 A1 | 6/2005 | Plewa et al. |
| 2005/0136258 A1 | 6/2005 | Nie et al. |
| 2005/0158390 A1 | 7/2005 | Rana et al. |
| 2005/0191294 A1 | 9/2005 | Arap et al. |
| 2005/0207940 A1 | 9/2005 | Butler |
| 2005/0214378 A1 | 9/2005 | Hoarau |
| 2005/0233948 A1 | 10/2005 | D'Amico et al. |
| 2005/0244863 A1 | 11/2005 | Mir |
| 2005/0249079 A1 | 11/2005 | Jacob et al. |
| 2005/0256071 A1 | 11/2005 | Davis et al. |
| 2005/0260186 A1 | 11/2005 | Bookbinder et al. |
| 2006/0002852 A1 | 1/2006 | Saltzman et al. |
| 2006/0002971 A1 | 1/2006 | Saltzman |
| 2006/0004042 A1 | 1/2006 | Dalton et al. |
| 2006/0009529 A1 | 1/2006 | Dalton et al. |
| 2006/0035966 A1 | 2/2006 | Dalton et al. |
| 2006/0057219 A1 | 3/2006 | Nagasaki et al. |
| 2006/0062787 A1 | 3/2006 | Hitraya |
| 2006/0083711 A1 | 4/2006 | Berry et al. |
| 2006/0110460 A1 | 5/2006 | Ferret et al. |
| 2006/0111271 A1 | 5/2006 | Cerny et al. |
| 2006/0165987 A1 | 7/2006 | Hildgen et al. |
| 2006/0173170 A1 | 8/2006 | Chamberlain et al. |
| 2006/0183931 A1 | 8/2006 | Dalton et al. |
| 2006/0228371 A1 | 10/2006 | Raso |
| 2006/0239907 A1 | 10/2006 | Luzzi et al. |
| 2006/0240093 A1 | 10/2006 | Maclachlan et al. |
| 2006/0241180 A1 | 10/2006 | Dalton et al. |
| 2006/0258628 A1 | 11/2006 | Steiner et al. |
| 2006/0269557 A1 | 11/2006 | Sherman et al. |
| 2006/0276540 A1 | 12/2006 | Dalton et al. |

(56) References Cited

U.S. PATENT DOCUMENTS

| | | |
|---|---|---|
| 2006/0287547 A1 | 12/2006 | Dalton et al. |
| 2007/0014807 A1 | 1/2007 | Maida et al. |
| 2007/0041901 A1 | 2/2007 | Diener et al. |
| 2007/0043066 A1 | 2/2007 | Sum et al. |
| 2007/0053845 A1 | 3/2007 | Sengupta |
| 2007/0116768 A1 | 5/2007 | Chorny et al. |
| 2007/0184068 A1 | 8/2007 | Renner et al. |
| 2007/0224225 A1 | 9/2007 | IracheGarreta |
| 2007/0225213 A1 | 9/2007 | Kosak |
| 2008/0026000 A1 | 1/2008 | Ennifar |
| 2008/0031899 A1 | 2/2008 | Reddy |
| 2008/0057102 A1 | 3/2008 | Roorda et al. |
| 2008/0081074 A1 | 4/2008 | Gu et al. |
| 2008/0124400 A1 | 5/2008 | Liggins et al. |
| 2008/0171059 A1 | 7/2008 | Howland |
| 2008/0193381 A1 | 8/2008 | Babich et al. |
| 2008/0213377 A1 | 9/2008 | Bhatia et al. |
| 2008/0268063 A1 | 10/2008 | Jon et al. |
| 2008/0299177 A1 | 12/2008 | Hardy |
| 2009/0004118 A1 | 1/2009 | Nie |
| 2009/0028910 A1 | 1/2009 | DeSimone et al. |
| 2009/0061010 A1 | 3/2009 | Zale et al. |
| 2009/0074828 A1 | 3/2009 | Alexis |
| 2009/0117549 A1 | 5/2009 | Tan |
| 2009/0192100 A1 | 7/2009 | Vater |
| 2009/0298710 A1 | 12/2009 | Farokhzad et al. |
| 2010/0022680 A1 | 1/2010 | Karnik et al. |
| 2010/0068285 A1 | 3/2010 | Zale et al. |
| 2010/0068286 A1 | 3/2010 | Troiano et al. |
| 2010/0069426 A1 | 3/2010 | Zale et al. |
| 2010/0092425 A1 | 4/2010 | Von Andrian et al. |
| 2010/0104655 A1 | 4/2010 | Zale et al. |
| 2010/0129392 A1 | 5/2010 | Shi et al. |
| 2010/0129439 A1 | 5/2010 | Alexis et al. |
| 2010/0144845 A1 | 6/2010 | Farokhzad et al. |
| 2010/0183727 A1 | 7/2010 | Iannaconne et al. |
| 2010/0196482 A1 | 8/2010 | Radovic-Moreno et al. |
| 2010/0203142 A1 | 8/2010 | Zhang et al. |
| 2010/0216804 A1 | 8/2010 | Zale et al. |
| 2010/0226986 A1 | 9/2010 | Grayson |
| 2010/0233251 A1 | 9/2010 | Von Andrian et al. |
| 2010/0266491 A1 | 10/2010 | Farokhzad et al. |
| 2010/0297233 A1 | 11/2010 | Moretti et al. |
| 2010/0303723 A1 | 12/2010 | Farokhzad et al. |
| 2011/0052697 A1 | 3/2011 | Farokhzad et al. |

FOREIGN PATENT DOCUMENTS

| | | |
|---|---|---|
| DK | 0418187 | 3/1991 |
| EP | 0333523 | 9/1989 |
| EP | 1279404 | 1/2003 |
| EP | 1752141 | 2/2007 |
| EP | 1872793 | 1/2008 |
| EP | 1932538 | 6/2008 |
| EP | 2106806 | 10/2009 |
| KR | 0418916 | 3/2002 |
| KR | 0041712 | 6/2004 |
| WO | WO 88/04300 | 6/1988 |
| WO | WO 90/11364 | 3/1990 |
| WO | WO 90/06430 | 6/1990 |
| WO | WO 90/06433 | 6/1990 |
| WO | WO 91/06286 | 5/1991 |
| WO | WO 91/06287 | 5/1991 |
| WO | WO 95/03357 | 2/1995 |
| WO | WO 97/04747 | 2/1997 |
| WO | WO 97/13537 | 4/1997 |
| WO | WO 97/37705 | 10/1997 |
| WO | WO 98/08856 | 3/1998 |
| WO | WO 98/51325 | 11/1998 |
| WO | WO 99/01498 | 1/1999 |
| WO | WO 99/34850 | 7/1999 |
| WO | WO 00/21572 | 4/2000 |
| WO | WO 00/27363 | 5/2000 |
| WO | 0032239 | 6/2000 |
| WO | WO 00/44895 | 8/2000 |
| WO | WO 01/75164 | 10/2001 |
| WO | WO 02/18477 | 3/2002 |
| WO | WO 02/076469 | 10/2002 |
| WO | WO 02/076603 | 10/2002 |
| WO | WO 02/100442 | 12/2002 |
| WO | WO 03/000777 | 1/2003 |
| WO | WO 03/004654 | 1/2003 |
| WO | WO 03/028657 | 4/2003 |
| WO | WO 03/030941 | 4/2003 |
| WO | WO 03033592 | 4/2003 |
| WO | WO 03/051304 | 6/2003 |
| WO | 03074679 | 9/2003 |
| WO | WO 03/072637 | 9/2003 |
| WO | WO 03/102708 | 12/2003 |
| WO | 2004030608 | 4/2004 |
| WO | WO 2004/030608 | 4/2004 |
| WO | WO 2004/071493 | 8/2004 |
| WO | WO 2004/096140 | 11/2004 |
| WO | WO 2004/096998 | 11/2004 |
| WO | 2004105782 | 12/2004 |
| WO | WO 2005/012407 | 2/2005 |
| WO | WO 2005/028539 | 3/2005 |
| WO | WO 2005/042573 | 5/2005 |
| WO | WO 2005/046572 | 5/2005 |
| WO | WO 2005/072710 | 8/2005 |
| WO | WO 2005/105056 | 11/2005 |
| WO | WO 2005/111192 | 11/2005 |
| WO | 2005112885 | 12/2005 |
| WO | WO 2005/112886 | 12/2005 |
| WO | WO 2005/121181 | 12/2005 |
| WO | WO 2006/025627 | 3/2006 |
| WO | WO 2006/037979 | 4/2006 |
| WO | WO 2006/042146 | 4/2006 |
| WO | WO 2006/066158 | 6/2006 |
| WO | WO 2006/078278 | 7/2006 |
| WO | WO 2006/090924 | 8/2006 |
| WO | WO 2006/093991 | 9/2006 |
| WO | WO 2006/096754 | 9/2006 |
| WO | WO 2006/099445 | 9/2006 |
| WO | WO 2006/117217 | 11/2006 |
| WO | WO 2006/133271 | 12/2006 |
| WO | WO 2006/138463 | 12/2006 |
| WO | WO 2007/001448 | 1/2007 |
| WO | WO 2007/021142 | 2/2007 |
| WO | 2007024026 | 3/2007 |
| WO | WO 2007/034479 | 3/2007 |
| WO | WO 2007/070682 | 6/2007 |
| WO | WO 2007/076371 | 7/2007 |
| WO | WO 2007/084797 | 7/2007 |
| WO | 2007098254 | 8/2007 |
| WO | WO 2007/098254 | 8/2007 |
| WO | WO 2007/109364 | 9/2007 |
| WO | WO 2007/118653 | 10/2007 |
| WO | WO 2007/133807 | 11/2007 |
| WO | WO 2007/144807 | 12/2007 |
| WO | WO 2007/150030 | 12/2007 |
| WO | WO 2008/019142 | 2/2008 |
| WO | WO 2008/041703 | 4/2008 |
| WO | WO 2008/051291 | 5/2008 |
| WO | WO 2008/058192 | 5/2008 |
| WO | WO 2008/105772 | 9/2008 |
| WO | WO 2008/121949 | 10/2008 |
| WO | WO 2009/051837 | 4/2009 |
| WO | WO 2009/109428 | 9/2009 |
| WO | WO 2010/005721 | 1/2010 |
| WO | WO 2010/005723 | 1/2010 |
| WO | WO 2010/005725 | 1/2010 |
| WO | WO 2010/005726 | 1/2010 |
| WO | WO 2010/068866 | 6/2010 |
| WO | WO 2010/075072 | 7/2010 |
| WO | WO 2010/114768 | 10/2010 |
| WO | WO 2010/114770 | 10/2010 |
| WO | WO 2011/072218 | 6/2011 |

OTHER PUBLICATIONS

Foss, et al., "Radiolabeled small-molecule ligands for prostate-specific membrane antigen; in vivo imaging in experimental models of prostate cancer", Clin. Cancer Res., 11:4022-28 (2005).

(56) References Cited

OTHER PUBLICATIONS

Govender, et al., "Defining the drug incorporation properties of PLA-PEG nanoparticles", Intl J of Pharmaceutics, 1999:95-110(2000).
Mitra, et al., "Tumour targeted delivery of encapsulated dextran-doxorubicin conjugate using chitosan nanoparticles as carrier", J Controlled Release, 74:317-23 (2001).
Wu, et al., ng-circulation Poly(ethylene glycol)-poly(D,L-lactide) block copolymermicelles with modulated surace chane, J Contl Rel., 77:27-38 (2001).
Zhou, et al., "NAAG peptidase inhibitors and their potential for diagnosis and therapy", Nature Rev. Drug Disc., 4:1015-26 (2005).
U.S. Appl. No. 12/239,136, filed Sep. 26, 2008, Farokhzad, et al.
U.S. Appl. No. 12/301,225, filed Nov. 17, 2008, Farokhzad, et al.
U.S. Appl. No. 12/515,465, filed May 5, 2010, Farokhzad, et al.
Abad, et al, "Comparison of a Monoclonal Antibody-Based Enzyme-Linked Immunosorbent Assay and Gas Chromatography for the Determination of Nicotine in Cigarette Smoke Condensates", Anal. Chem., 65:3227-3231 (1993).
Ackermand & Cresswell, "Cellular mechanisms governing cross-presentation of exogenous antigens", Nat. Immunol., 5(7):678-684 (2004).
Aime, et al., "Lanthanide(III) chelates for NMR biomedical applications", Chemical Society Reviews, 27:19-29 (1998).
Akaishi, et al., "Targeting Chemotherapy Using Antibody-Combined Liposome against Human Pancreatic Cancer Cell-Line", Tohoku J. Exp. Med., 175(1):29-42 (1995).
Allen, et al., "Nano-engineering block copolymer aggregates for drug delivery.", Colloids Surfaces B-Biointerfaces, 16:3-27 (1999).
Allison, et al., "The mode of action of immunological adjuvants.", Dev. Biol. Stand., 92:3-11 (1998).
Altschul, et al., "Basic local alignment search tool.", J. Mol Biol., 215(3):403-10 (1990).
Altschul, et al., "Gapped BLAST and PSI-BLAST: a new generation of protein database search programs.", Nucleic Acids Res., 25(17):3389-3402 (1997).
Angelucci, et al., "Neuroendocrine transdifferentiation induced by VPA is mediated by PPARγ activation and confers resistance to antiblastic therapy in prostate carcinoma", The Prostate, 68(6):588-598 (2008).
Astete and Sabliov, "Synthesis and characterization of PLGA nanoparticles", J. Biomat. Sci.,-Polyner Ed., 17:247-289 (2006).
Atkinson, et al., "Conjugation of folate via gelonin carbohydrate residues retains ribosomal-inactivating properties of the toxin and permits targeting to folate receptor positive cells.", J. Biol. Chem., 276(30):27930-27935 (2001).
Baba, et al., "Human neutralizing monoclonal antibodies of the IgG1 subtype protect against mucosal simian-human immunodeficiency virus infection.", Nat. Med., 6(2):200-206 (2000).
Babaian, et al., "Radioimmunological imaging of metastatic prostatic cancer with 111indium-labeled monoclonal antibody PAY 276.", J. Urol., 137(3):439-443 (1987).
Bachmann, et al., "T helper cell-independent neutralizing B cell response against vesicular stomatitis virus: role of antigen patterns in B cell induction?", Eur. J. Immunol., 25(12):3445-3451 (1995).
Bagalkot, et al., "An Aptamer-Doxorubicin Physical Conjugate as a Novel Targeted Drug-Delivery Platform", Angew. Chem. Int. Ed., 45(48):8149-8152 (2006).
Bander, et al., "Targeting metastatic prostate cancer with radiolabeled monoclonal antibody J591 to the extracellular domain of prostate specific membrane antigen.", J. Urol., 170(5):1717-1721 (2003).
Barchet, et al., "Virus-induced interferon alpha production by a dendritic cell subset in the absence of feedback signaling in vivo.", J. Exp. Med., 195(4):507-516 (2002).
Barrera, et al., "Synthesis and RGD peptide modification of a new biodegradable copolymer: poly(lactic acid-co-lysine)", J. Am. Chem. Soc., 115(23):11010-11011 (1993).
Bauer, et al., "SMS 201-995: a very potent and selective octapeptide analogue of somatostatin with prolonged action.", Life Sci., 31(11):1133-1140 (1982).

Beaureparie, et al., "Functionalized Fluorescent Oxide Nanoparticles: Artificial Toxins for Sodium Channel Targeting and Imaging at the Single-Molecule Level", Nano Letters, 4(11):2079-2083 (2004).
Bennett, et al., "Inhibition of the Aminopeptidase from Aeromonas Proteolytica by I-Leucinephosphonic Acid, a Transistion State Analogue of Peptide Hydrolysis", J. Am. Chem. Soc., 120(46):12139-12140 (1998).
Binetruy-Tournaire, et al., "Identification of a peptide blocking vascular endothelial growth factor (VEGF)-mediated angiogenesis.", EMBO J., 19(7):1525-1533 (2000).
Bjerke, et al., "Comparison of monoclonal and polyclonal antibodies to continine in nonisotopic and isotopic immunoassays", J. Immunol. Meth., 96:239-246 (1987).
Boes, et al., "T-cell engagement of dendritic cells rapidly rearranges MHC class II transport.", Nature, 418(6901):983-988 (2002).
Bonifaz, et al., "Efficient targeting of protein antigen to the dendritic cell receptor DEC-205 in the steady state leads to antigen presentation on major histocompatibility complex class I products and peripheral CD8+ T cell tolerance.", J. Exp. Med., 196(12):1627-1638 (2002).
Bottausci, et al., "Mixing in the shear superposition micromixer: three-dimensional analysis", Philosophical Transactions of the Royal Society of London Series a—Mathematical Physical and Engineering Sciences, 362:1001-1018 (2004).
Boussif, et al., "A versatile vector for gene and oligonucleotide transfer into cells in culture and in vivo: polyethylenimine.", Proc. Natl. Acad. Sci., USA, 1995, 92:7297-7301 (1995).
Bozzacco, et al., "DEC-205 receptor on dendritic cells mediates presentation of HIV gag protein to CD8+ T cells in a spectrum of human MHC I haplotypes.", Proc. Natl. Acad. Sci., USA, 104(4):1289-1294 (2007).
Brito, et al., "Nanoparticulate carriers for the treatment of coronary restenosis.", Int J Nanomedicine, 2(2):143-161 (2007).
Burmeister, et al., "Direct in vitro selection of a 2'-O-methyl aptamer to VEGF.", Chem Biol, 12(1):25-33 (2005).
Carino, et al., "Nanosphere based oral insulin delivery," J. Control. Release, 65(1-2):261-9 (2000).
Casola, et al., "B cell receptor signal strength determines B cell fate.", Nat. Immunol., 5(3):317-327 (2004).
Castro & Prieto, "Nicotine Antibody Production: Comparison of two nicotine conjugates in different animal species", Biochem. Biophys. Res. Comm., 67(2):583-589 (1975).
Castro, et al., "Nicotine Antibodies: Comparison of Ligand Specificities of Antibodies Produced against Two Nicotine Conjugates", Eur. J. Biochem., 104:331-340 (1980).
Chacon, et al., "Optimized preparation of poly D,L (lactic-glycolic) microspheres and nanoparticles for oral administration", Int'l J. Pharmaceutics, 141:81-91 (1996).
Chaires, et al., "Preferential binding of daunomycin to 5'ATCG and 5'ATGC sequences revealed by footprinting titration experiments.", Biochemistry, 29(26):6145-6153 (1990).
Chang, et al., "Five Different Anti-Prostate-specific Membrane Antigen (PSMA) Antibodies Confirm PSMA Expression in Tumor-associated Neovasculature", Cancer Res., 59:3192-3198 (1999).
Cheng, et al., "Formulation of functionalized PLGA-PEG nanoparticles for in vivo targeted drug delivery.", Biomaterials, 28(5):869-876 (2007).
Christian, et al., "Nucleolin expressed at the cell surface is a marker of endothelial cells in angiogenic blood vessels.", J. Cell Biol., 163(4):871-878 (2003).
Chu, et al., "Aptamer mediated siRNA delivery", Nuc. Acid Res., 34:e73 (2006).
Chu, et al., "Labeling tumor cells with fluorescent nanocrystal-aptamer bioconjugates.", Biosens. Bioelectron., 21:1859-1866 (2006).
Clark, "The reticulum of lymph nodes in mice studied with the electron microscope.", Am. J. Anat., 110:217-257 (1962).
Connor, et al., "Ex vivo evaluation of anti-EpCAM immunocytokine huKS-IL2 in ovarian cancer.", J. Immunother., 27(3):211-219 (2004).
Croy and Kwon, "Polymeric micells for drug delivery", Curr. Pharm. Design, 12:4669-4684 (2006).

(56) References Cited

OTHER PUBLICATIONS

D'Antonio, et al., "Longitudinal analysis of androgen deprivation of prostate cancer cells identifies pathways to androgen independence", *The Prostate*, 68(7):698-714 (2008).

Dang and Rock, "Stimulation of B lymphocytes through surface Ig receptors induces LFA-1 and ICAM-1-dependent adhesion.", *J. Immunol.*, 146(10):3273-3279 (1991).

De Graaf, et al., "A fully human anti-Ep-CAM scFv-beta-glucuronidase fusion protein for selective chemotherapy with a glucuronide prodrug.", *Br. J. Cancer*, 86(5):811-818 (2002).

De Jaeghere, et al., "Freeze-drying and lyopreservation of diblock and triblock poly(lactic acid)-poly(ethylene oxide) (PLA-PEO) copolymer nanoparticles.", *Pharm. Dev. Technol.*, 5(4):473-483 (2000).

Delemarre, et al., "Repopulation of macrophages in popliteal lymph nodes of mice after liposome-mediated depletion.", *J. Leukoc. Biol.*, 47(3):251-257 (1990).

Demello and Demello, "Microscale reactors: nanoscale products.", *Lab on a Chip*, 4(2):11N-15N (2004).

Demello, "Control and detection of chemical reactions in microfluidic systems.", *Nature*, 442(7101):394-402 (2006).

Deming, et al., "Facile synthesis of block copolypeptides of defined architecture.", *Nature*, 390(6658):386-389 (1997).

Derfus, et al., "Intracellular Delivery of Quantum Dots for Live Cell Labeling and Organelle Tracking", *Advanced Materials*, 16:961-966 (2004).

Dimarco and Arcamone, "DNA complexing antibiotics: Daunomycin, adriamycin and their derivates.", *Arzneim-Forsch. (Drug Res.)*, 25:368-375 (1975).

Ding, et al., "Syntheses of conformationally constricted molecules as potential NAALADase/PSMA inhibitors.", *Org. Lett.*, 6(11):1805-1808 (2004).

Dinkla, et al., "Identification of a streptococcal octapeptide motif involved in acute rheumatic fever.",*J. Biol. Chem.*, 282(26):18686-18693 (2007).

Dykxhoorn, et al., "Killing the messenger: short RNAs that silence gene expression.", *Nat. Rev. Mol. Cell Biol.*, 4(6):457-467 (2003).

Eklund, et al., "Denileukin diftitox: a concise clinical review.", *Expert Rev. Anticancer Ther.*, 5(1):33-38 (2005).

Elbashir, et al., "RNA interference is mediated by 21- and 22-nucleotide RNAs.", *Genes Dev.*, 15(2):188-200 (2001).

Eldridge, et al., "Biodegradable microspheres as a vaccine delivery system," *Mol. Immunol.*, 28(3):287-94 (1991).

Elsässer-Beile, et al., "A new generation of monoclonal and recombinant antibodies against cell-adherent prostate specific membrane antigen for diagnostic and therapeutic targeting of prostate cancer.", *Prostate*, 66(13):1359-1370 (2006).

Farokhzad, et al., "Nanoparticle-Aptamer Bioconjugates: A New Approach for Targeting Prostate Cancer Cells," *Cancer Research*, 64:7668-7672 (2004).

Farokhzad, et al., "Nanoparticle—aptamer bioconjugates for cancer targeting", *Expert Opin. Drug Delivery*, 3(3):311-324 (2006).

Farokhzad, et al., "Targeted nanoparticle—aptamer bioconjugates for cancer chemotherapy in vivo.", *Proc. Natl. Acad. ScL, USA*, 103(16):6315-6320 (2006).

Farr, et al., "The structure of the sinus wall of the lymph node relative to its endocytic properties and transmural cell passage.", *Am. J. Anat.*, 157(3):265-284 (1980).

Fire, et al., "Potent and specific genetic interference by double-stranded RNA in Caenorhabditis elegans.", *Nature*, 391(6669):806-811 (1998).

Fonseca, et al., "Paclitaxel-loaded PLGA nanopartides: preparation, physicochemical characterization and in vitro anti-tumoral activity.", *J. Control. Release*, 83(2):273-286 (2002).

Fracasso, et al., "Anti-tumor effects of toxins targeted to the prostate specific membrane antigen.", *Prostate*, 53(1):9-23 (2002).

Francis, et al., "A phase I trial of antibody directed enzyme prodrug therapy (ADEPT) in patients with advanced colorectal carcinoma or other CEA producing tumours.", *Br. J. Cancer*, 87(6):600-607 (2002).

Frankel, et al., "Phase I trial of a novel diphtheria toxin/granulocyte macrophage colony-stimulating factor fusion protein (DT388GMCSF) for refractory or relapsed acute myeloid leukemia.", *Clin. Cancer Res.*, 8(5):1004-1013 (2002).

Frederick, et al., "Structural comparison of anticancer drug-DNA complexes: adriamycin and daunomycin.", *Biochemistry*, 29(10):2538-2549 (1990).

Froidevaux, et al., "Somatostatin analogs and radiopeptides in cancer therapy.", *Biopolymers*, 66(3):161-183 (2002).

Fujita, et al., "Cytokine profiling of prostatic fluid from cancerous prostate glands identifies cytokines associated with extent of tumor and inflammation", *The Prostate*, 68(8):872-882 (2008).

Gao, et al., "A method for the generation of combinatorial antibody libraries using pIX phage display," *Proc. Natl. Acad. Sci. U.S.A.*, 99(20): 12612-6 (2002).

Gao, et al., "In vivo cancer targeting and imaging with semiconductor quantum dots.", *Nat. Biotechnol.*, 22(8):969-976 (2004).

Gao, et al., "In vivo molecular and cellular imaging with quantum dots.", *Curr. Op. Biotechnol.*, 16:63-72 (2005).

Gershlick, "Treating atherosclerosis: local drug delivery from laboratory studies to clinical trials," *Atherosclerosis*, 160(2): 259-71 (2002).

Gillies, et al., "An anti-CD20-IL-2 immunocytokine is highly efficacious in a SCID mouse model of established human B lymphoma.", *Blood*, 105(10):3972-3978 (2005).

Grauer, et al., "Identification, purification, and subcellular localization of prostate-specific membrane antigen PSM protein in the LNCaP prostatic carcinoma cell line.", *Cancer Res.*, 58(21):4787-4789 (1998).

Gref, et al., "Biodegradable long-circulating polymeric nanospheres.", *Science*, 263(5153):1600-1603 (1994).

Haensler, et al., "Polyamidoamine cascade polymers mediate efficient transfection of cells in culture", *Bioconjugate Chem.*, 4(5):372-379 (1993).

Haj, et al., "New findings in the study on the intercalation of bisdaunorubicin and its monomeric analogues with naked and nucleus DNA.", *Chem. Biol. Interact.*, 145(3):349-358 (2003).

Hanes, et al., "Polymer microspheres for vaccine delivery.", *Pharm. Biotechnol.*, 6:389-412 (1995).

Hangartner, et al., "Antiviral immune responses in gene-targeted mice expressing the immunoglobulin heavy chain of virus-neutralizing antibodies.", *Proc. Natl. Acad. Sci., USA*, 100:12883-12888 (2003).

Hannon, et al., "Unlocking the potential of the human genome with RNA interference", *Nature*, 431(7006):371-378 (2004).

Harada and Kataoka, "Supramolecular assemblies of block copolymers in aqueous media as nanocontainers relevant to biological applications", *Progress Polymer Sci.*, 31(11):949-982 (2006).

Harper, et al., "Efficacy of a bivalent L1 virus-like particle vaccine in prevention of infection with human papillomavirus types 16 and 18 in young women: a randomised controlled trial.", *Lancet*, 364(9447)1757-1765 (2004).

Haseloff and Gerlach, "Simple RNA enzymes with new and highly specific endoribonuclease activities.", *Nature*, 334(6183):585-591 (1988).

Hawiger, et al., "Dendritic cells induce peripheral T cell unresponsiveness under steady state conditions in vivo.", *J. Exp. Med.* 194(6):769-779 (2001).

He, et al., "A microRNA polycistron as a potential human oncogene," *Nature*, 435(7043): 828-833 (2005).

Hélène "The anti-gene strategy: control of gene expression by triplex-forming-oligonucleotides.", *Anticancer Drug Des.* 6(6):569-584 (1991).

Helene, et al., "Control of gene expression by triple helix-forming oligonucleotides. The antigene strategy.", *Ann, N.Y. Acad. Sci.* 660:27-36 (1992).

Hermann and Patel, "Adaptive recognition by nucleic acid aptamers," *Science*, 287: 820-825 (2000).

Hieda, et al., "Active Immunization Alters the Plasma Nicotine Concentration in Rats", *J. Pharmacol. Exp. Therapeutics*, 283:1076-1081 (1997).

Hieda, et al., "Immunization of rats reduces nicotine distribution to brain", *Psychopharmacology*, 143:150-157 (1999).

(56) References Cited

OTHER PUBLICATIONS

Horoszewicz, et al., "Monoclonal antibodies to a new antigenic marker in epithelial prostatic cells and serum of prostatic cancer patients.", *Anticancer Res.*, 7(5B):927-935 (1987).
Houghton, "General method for the rapid solid-phase synthesis of large numbers of peptides: Specificity of antigen-antibody interaction at the level of individual amino acids", *Immunol.*, 82:5131-5135 (1985).
Jackson, et al., "Design and pharmacological activity of phosphinic acid based NAALADase inhibitors.", *J. Med. Chem.*, 44(24):4170-4175 (2001).
Jackson, et al., "Design of NAALADase inhibitors: a novel neuroprotective strategy.", *Curr. Med. Chem.*, 8(8):949-957 (2001).
Johnson and Prud'Homme, "Mechanism for rapid self-assembly of block copolymer nanoparticles.", *Phys. Rev. Lett.*, 91(11):118302 (2003).
Jones and Leroux, "Polymeric micelles—a new generation of colloidal drug carriers", *Eur. J. Pharmaceutics Biopharmaceutics*, 48:101-111 (1999).
Jung, et al., "Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice", *Pharmaceutical Research*, 18(3):352-360 (2001).
Junt, et al., "Subcapsular sinus macrophages in lymph nodes clear lymph-borne viruses and present them to antiviral B cells", *Nature*, 450:110-116 (2007).
Kabanov, et al., "DNA Complexes with Polycations for the Delivery of Genetic Material into Cells", *Bioconjugate Chem.*, 6(1):7-20 (1995).
Kamentsky, "Laser scanning cytometry.", *Methods Cell Biol.*, 63:51-87 (2001).
Kanashiro, et al., "Inhibition of mutant p53 expression and growth of DMS-153 small cell lung carcinoma by antagonists of growth hormone-releasing hormone and bombesin.", *Proc. Natl. Acad. Sci., USA*, 100(26):15836-15841 (2003).
Karlin and Altschul, "Applications and statistics for multiple high-scoring segments in molecular sequences.", *Proc. Natl Acad. Sci. USA*, 90(12):5873-5877 (1993).
Karlin and Altschul, "Methods for assessing the statistical significance of molecular sequence features by using general scoring schemes.", *Proc. Natl Acad Sci. USA*, 87:2264-2268 (1990).
Karrer, et al., "On the key role of secondary lymphoid organs in antiviral immune responses studied in alymphoplastic (aly/aly) and spleenless (Hox11(-)/-) mutant mice.", *J. Exp. Med.*, 185(12):2157-2170 (1997).
Kelly, et al., "The Optical Properties of Metal Nanopartieles: The Influence of Size, Shape, and Dielectric Environment", *J. Phys. Chem. B.*, 107(3):668-677 (2003).
Khademhosseini, et al., "Cell docking inside microwells within reversibly sealed microfluidic channels for fabricating multiphenotype cell arrays," *Lab Chip*, 5(12):1380-6 (2005).
Knight, et al., "Hydrodynamic Focusing on a Silicon Chip: Mixing Nanoliters in Microseconds", *Phys. Rev. Lett.*, 80:3863-3866 (1998).
Köhrer and Rajbhandary, "Proteins carrying one or more unnatural amino acids," In Ibba, et al., (eds.), *Aminoacyl-tRNA Synthetases*, Landes Bioscience, Chapter 31 (2005).
Köhrer, et al., "Complete set of orthogonal 21st aminoacyl-tRNA synthetase-amber, ochre and opal suppressor tRNA pairs: concomitant suppression of three different termination codons in an mRNA in mammalian cells.", *Nucleic Acids Res.*, 32(21):6200-6211 (2004).
Köhrer, et al., "Import of amber and ochre suppressor tRNAs into mammalian cells: a general approach to site-specific insertion of amino acid analogues into proteins.", *Proc. Natl. Acad. Sci., USA*, 98(25):14310-14315 (2001).
Koivunen, et al., "Phage libraries displaying cyclic peptides with different ring sizes: ligand specificities of the RGD-directed integrins.", *Biotechnology* (NY), 13(3):265-270 (1995).
Koivunen, et al., "Tumor targeting with a selective gelatinase inhibitor", *Nat. Biotechnol.*, 17:768-774 (1999).
Konan, et al., "Preparation and characterization of sterile sub-200 nm meso-tetra(4-hydroxylphenyl)porphyrin-loaded nanoparticles for photodynamic therapy", *Eur. J. Pharmaceutics Biopharmaceutics*, 55:115-124 (2003).
Kozikowski, et al., "Synthesis of urea-based inhibitors as active site probes of glutamate carboxypeptidase II: efficacy as analgesic agents.", *J. Med. Chem.*, 47(7):1729-1738 (2004).
Krieg, et al., "CpG motifs in bacterial DNA trigger direct B-cell activation.", *Nature*, 374(6522):546-549 (1995).
Kreitman, et al., "Efficacy of the anti-CD22 recombinant immunotoxin BL22 in chemotherapy-resistant hairy-cell leukemia.", *N. Engl J. Med.*, 345(4):241-347 (2001).
Kreitman, et al., "Phase I trial of recombinant immunotoxin anti-Tac(Fv)-PE38 (LMB-2) in patients with hematologic malignancies.", *J. Clin. Oncol.*, 18(8):1622-1636 (2000).
Kukowska-Latallo, et al., "Efficient transfer of genetic material into mammalian cells using Starburst polyamidoamine dendrimers", *Proc. Natl. Acad. Sci., USA*, 93(10):4897-4902 (1996).
Kumar, et al., "Inhibition of angiogenesis and tumor growth by SCH221153, a dual alpha(v)beta3 and alpha(v)beta5 integrin receptor antagonist.", *Cancer Res.*, 61(5):2232-2238 (2001).
Kwon, et al., "Pseudopoly(amino acids): study of the synthesis and characterization of poly(acyl-hydroxyproline-esters)", *Macromolecules*, 22:3250-3255 (1989).
Laakkonen, et al., "Antitumor activity of a homing peptide that targets tumor lymphatics and tumor cells.", *Proc. Natl. Acad. Sci., USA*, 101(25):9381-9386 (2004).
Labhasetwar, et al., "Arterial uptake of biodegradable nanoparticles: Effect of surface modifications," *J. Pharm. Sci.*, 87(10): 1229-34 (1998).
Langer, "Biomaterials in drug delivery and tissue engineering: one laboratory's experience.", *Acc. Chem. Res.*, 33(2):94-101 (2000).
Langer, "New methods of drug delivery," *Science*, 249(4976):1527-33 (1990).
Langer, "Selected advances in drug delivery and tissue engineering", *J. Control. Release*, 62:7-11 (1999).
Langone, et al., "Nicotine and its metabolites. Radioimmunoassays for nicotine and cotinine", *Biochem.*, 12(24):5025-5030 (1973).
Langone & Van Vunakis, "Radioimmunoassay of Nicotine, Cotinine, and γ-(3-Pyridyl)-γ-oxo-N-methylbutyramide", *Met. Enzymol.*, 84:628-640 (1982).
Leamon, et al., "Cytotoxicity of folate-Pseudomonas exotoxin conjugates toward tumor cells. Contribution of translocation domain.", *J. Biol. Chem.*, 268(33):24847-24854 (1993).
Leamon, et al., "Selective targeting of malignant cells with cytotoxin-folate conjugates.", *J. Drug Target.*, 2(2):101-112 (1994).
Leopold, et al., "Fluorescent virions: dynamic tracking of the pathway of adenoviral gene transfer vectors in living cells.", *Human Gene Therapy*, 9(3):367-378 (1998).
Leroy, et al., "Radioimmunodetection of lymph node invasion in prostatic cancer. The use of iodine 123 (123I)-labeled monoclonal anti-prostatic acid phosphatase (PAP) 227 A F(ab')2 antibody fragments in vivo.", *Cancer*, 64(1):1-5 (1989).
Leucuta, et al., "Albumin microspheres as a drug delivery system for epirubicin: pharmaceutical, pharmacokinetic and biological aspects," *International Journal of Pharmaceutics*, 41: 213-7 (1988).
Lim, et al., "A Self-Destroying Polycationic Polymer: Biodegradable Poly(4-hydroxy-l-proline ester)", *J. Am. Chem. Soc.*, 121(24):5633-5639 (1999).
Lim, et al., "Cationic hyperbranched poly(amino ester): a novel class of DNA condensing molecule with cationic surface, biodegradable three-dimensional structure, and tertiary amine groups in the interior.", *J. Am. Chem. Soc*, 123(10):2460-2461 (2001).
Lin, et al., "A microRNA polycistron as a potential human oncogene p828", *Nature*, 435(7043):828-833 (2005).
Lin, et al., "Well-Ordered Mesoporous Silica Nanoparticles as Cell Markers", *Chem. Mater.*, 17:4570-4573 (2005).
Liu, et al., "Cell-Surface labeling and internalization by a fluorescent inhibitor of prostate-specific membrane antigen", *The Prostate*, 68(9):955-964 (2008).
Liu, et al., "Constitutive and antibody-induced internalization of prostate-specific membrane antigen.", *Cancer Res.*, 58(18):4055-4060 (1998).

(56) References Cited

OTHER PUBLICATIONS

Liu, et al., "Folate-targeted enzyme prodrug cancer therapy utilizing penicillin-V amidase and a doxorubicin prodrug.", *J. Drug Target.*, 7:43-53 (1999).

Liu, et al., "Hypermethylation of MCAM gene is associated with advanced tumor stage in prostate cancer", *The Prostate*, 68(4):418-426 (2008).

Liu, et al., "Monoclonal antibodies to the extracellular domain of prostate-specific membrane antigen also react with tumor vascular endothelium.", *Cancer Res.*, 57(17):3629-3634 (1997).

Low, et al., "Folate receptor-targeted drugs for cancer and inflammatory diseases.", *Adv. Drug Deliv. Rev.*, 56(8):1055-1058 (2004).

Lu, et al., "MicroRNA expression profiles classify human cancers", *Nature*, 435(7043):834-838 (2005).

Ludewig, et al., "Induction of optimal anti-viral neutralizing B cell responses by dendritic cells requires transport and release of virus particles in secondary lymphoid organs.", *Eur. J. Immunol .,* 30(1):185-196 (2000).

Lupold, et al., "Identification and characterization of nuclease-stabilized RNA molecules that bind human prostate cancer cells via the prostate-specific membrane antigen.", *Cancer Res.*, 62(14):4029-4033 (2002).

Lyu, et al., "The immunocytokine scFv23/TNF sensitizes HER-2/neu-overexpressing SKBR-3 cells to tumor necrosis factor (TNF) via up-regulation of TNF receptor-1.", *Mol. Cancer Ther.*, 4(8):1205-1213 (2005).

Maher, "DNA triple-helix formation: An approach to artificial gene repressors?", *Bioassays* 14:807-815 (1992).

Majer, et al., "Synthesis and biological evaluation of thiol-based inhibitors of glutamate carboxypeptidase II: discovery of an orally active GCP II inhibitor.", *J. Med. Chem.*, 46(10):1989-1996 (2003).

Manolova, et al., "Nanoparticles target distinct dendritic cell populations according to their size", *Eur. J. Immunol.*, 38:1404-1413 (2008).

Manz, et al, "Capillary electrophoresis on a chip", *J. Chromatography*, 593:253-258 (1992).

Mathiowitz, et al., "Polyanhydride Microspheres as Drug Carriers I. Hot Melt Encapsulation", *J. Control. Release*, 5:13-22 (1987).

Mathiowitz, et al., "Novel microcapsules for delivery systems", *Reactive Polymers*, 6:275-283 (1987).

Mathiowitz, et al., "Polyanhydride Microspheres as Drug Carriers. II.Microencapsulation by Solvent Removal", *J. Appl. Polymer Sci.*, 35:755-774 (1988).

Mattheakis, et al., "Optical coding of mammalian cells using semiconductor quantum dots.", *Analytical Biochemistry*, 327(2):200-208 (2004).

Maung, et al., "Probing for a hydrophobic a binding register in prostate-specific membrane antigen with phenylalkylphosphonamidates.", *Bioorg. Med. Chem.*, 12(18):4969-4979 (2004).

McDevitt, et al., "An alpha-particle emitting antibody ([213Bi]J591) for radioimmunotherapy of prostate cancer.", *Cancer Res.*, 60(21):6095-6100 (2000).

McDevitt, et al., "Tumor therapy with targeted atomic nanogenerators.", *Science*, 294(5546):1537-1540 (2001).

Mead, et al., "Laboratory vector competence of black flies (Diptera:Simuliidae) for the Indiana serotype of vesicular stomatitis virus.", *Ann. N.Y. Acad. Sci.*, 916:437-443 (2000).

Meister, et al., "Mechanisms of gene silencing by double-stranded RNA.", *Nature*, 431(7006):343-349 (2004).

Melani, et al., "Targeting of interleukin 2 to human ovarian carcinoma by fusion with a single-chain Fv of antifolate receptor antibody.", *Cancer Res.*, 58(18):4146-4154 (1998).

Mempel, et al., "T-cell priming by dendritic cells in lymph nodes occurs in three distinct phases.", *Nature*, 427(6970):154-159 (2004).

Metelitsa, et al., "Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis.", *Blood*, 99(11):4166-4173 (2002).

Meyers, et al., "Development of monoclonal antibody imaging of metastatic prostatic carcinoma.", *Prostate*, 14(3):209-220 (1989).

Milligan and Uhlenbeck, "Synthesis of small RNAs using T7 RNA polymerase," *Methods in Enzymology*, 180: 51-62 (1989).

Moghimi, et al., "Long-circulating and target-specific nanoparticles: theory to practice," *Pharmacol. Rev.*, 53(2): 283-318 (2001).

Mulligan, "The basic science of gene therapy," *Science*, 260(5110):926-32 (1993).

Murphy, et al., "Isolation and characterization of monoclonal antibodies specific for the extracellular domain of prostate specific membrane antigen.", *J. Urol.*, 160(6 Pt 2):2396-2401 (1998).

Murray, et al., "Synthesis and characterization of monodisperse nanocrystals and close-packed nanocrystal assemblies", *Ann. Rev. Mat. Sci.*, 30:545-610 (2000).

Myers and Miller, *CABIOS* (1988).

Nan, et al., "Dual function glutamate-related ligands: discovery of a novel, potent inhibitor of glutamate carboxypeptidase II possessing mGluR3 agonist activity.", *J. Med. Chem.*, 43(5):772-774 (2000).

Neidle, "The molecular basis for the action of some DNA-binding drugs.", *Prog. Med. Chem.*, 16:151-221 (1979).

Nguyen and Wu, "Micromixers—a review.", *J. Micromechan. Microeng.*, 15:R1 (2005).

Notter, et al., "Targeting of a B7-1 (CD80) immunoglobulin G fusion protein to acute myeloid leukemia blasts increases their costimulatory activity for autologous remission T cells.", *Blood*, 97(10):3138-3145 (2001).

Ochsenbein, et al., "Protective T cell-independent antiviral antibody responses are dependent on complement.", *J. Exp. Med.*, 190(8):1165-1174 (1999).

Ochsenbein, et al., "Control of early viral and bacterial distribution and disease by natural antibodies.", *Science*, 286(5447):2156-2159 (1999).

O'Donnell, et al., "c-Myc-regulated microRNAs modulate E2F1 expression," *Nature*, 435(7043): 839-843 (2005).

Okada, et al., "Antigen-engaged B cells undergo chemotaxis toward the T zone and form motile conjugates with helper T cells.", *PLoS Biol.*, 3(6):e150 (2005).

Oliver, et al., "Conformational and SAR analysis of NAALADase and PSMA inhibitors.", *Bioorg. Med. Chem.*, 11(20):4455-4461 (2003).

Pape, et al., "The humoral immune response is initiated in lymph nodes by B cells that acquire soluble antigen directly in the follicles.", *Immunity*, 26(4):491-502 (2007).

Papisov, "Acyclic Polyacetals from Polysaccharides: Biomimetic Biomedical "Stealth" Polymers", *ACS Symposium Series*, 786:301-314 (2001).

Parekh, et al., "Biomarkers for Prostate Cancer Detection", *The Journal of Urology*, 178(6):2252-2259 (2007).

Pasqualini, et al., "Aminopeptidase N is a receptor for tumor-homing peptides and a target for inhibiting angiogenesis.", *Cancer Res.*, 60(3):722-727 (2000).

Patri, et al., "Synthesis and in Vitro Testing of J591 Antibody-Dendrimer Conjugates for Targeted Prostate Cancer Therapy", *Bioconj. Chem.*, 15:1174-1181 (2004).

Pellegrino, et al., "On the development of colloidal nanoparticles towards multifunctional structures and their possible use for biological applications.", *Small*, 1(1):48-63 (2005).

Pfohl, et al., "Trends in microfluidics with complex fluids.", *Chemphyschem*, 4(12):1291-1298 (2003).

Phillips, et al., "Enhanced antibody response to liposome-associated protein antigens: preferential stimulation of IgG2a/b production.", *Vaccine*, 10(3):151-158 (1992).

Porkka, et al., "A fragment of the HMGN2 protein homes to the nuclei of tumor cells and tumor endothelial cells in vivo.", *Proc. Natl. Acad. Sci., USA*, 99(11):7444-7449 (2002).

Putnam, et al., "Poly(4-hydroxy-l-proline ester): Low-Temperature Polycondensation and Plasmid DNA Complexation", *Macromolecules*, 32(11):3658-3662 (1999).

Qi, et al., "Extrafollicular activation of lymph node B cells by antigen-bearing dendritic cells", *Science*, 312(5780):1672-1676 (2006).

(56) References Cited

OTHER PUBLICATIONS

Quintanar-Guerrero, et al., "Preparation Techniques and Mechanisms of Formation of Biodegradable Nanoparticles from Preformed Polymers", *Drug Dev. Industrial Pharmacy*, 24(12):1113-1128 (1998).
Reddy, et al., "Exploiting lymphatic transport and complement activation in nanoparticle vaccines", *Nat. Biotech.*, 25(10):1159-1164 (2007).
Reif, et al., "Balanced responsiveness to chemoattractants from adjacent zones determines B-cell position.", *Nature*, 416(6876):94-99 (2002).
Reiher, et al., "Inhibition of tumor growth by systemic treatment with thrombospondin-1 peptide mimetics.", *Int. J. Cancer*, 98(5):682-689 (2002).
Reubi, et al., "Peptide receptors as molecular targets for cancer diagnosis and therapy.", *Endocr. Rev.*, 24(4):389-427 (2003).
Reynolds, et al., "Rational siRNA design for RNA interference.", *Nat. Biotechnol.*, 22(3):326-330 (2004).
Robbins, et al., "Stable expression of shRNAs in human CD34+ progenitor cells can avoid induction of interferon responses to siRNAs in vitro", *Nature Biotechnology*, 24(5):566-571 (2006).
Robinson, et al., "LEAPT: lectin-directed enzyme-activated prodrug therapy.", *Proc. Natl. Acad. Sci., USA*, 101(40):14527-14532 (2004).
Roost, et al., "Mapping of the dominant neutralizing antigenic site of a virus using infected cells.", *J. Immunol. Methods*, 189(2):233-242 (1996).
Rossbacher and Shlomchik, "The B cell receptor itself can activate complement to provide the complement receptor ½ ligand required to enhance B cell immune responses in vivo.", *J. Exp. Med.*, 198(4):591-602 (2003).
Sampson, et al., "Progress report of a Phase I study of the intracerebral microinfusion of a recombinant chimeric protein composed of transforming growth factor (TGF)-alpha and a mutated form of the Pseudomonas exotoxin termed PE-38 (TP-38) for the treatment of malignant brain tumors.", *J. Neurooncol.*, 65(1):27-35 (2003).
Santoyo, et al., "Highly specific and accurate selection of siRNAs for high-throughput functional assays.", *Bioinformatics*, 21(8):1376-1382 (2005).
Sarver, et al., "Ribozymes as potential anti-HIV-1 therapeutic agents.", *Science* 247(4947):1222-1225 (1990).
Schally, et al., "Peptide analogs in the therapy of prostate cancer.", *Prostate*, 45(2):158-166 (2000).
Schultz, "Plasmon resonant particles for biological detection", *Curr. Op. Biotechnol.*, 14:13-22 (2003).
Schultz, et al., "Single-target molecule detection with nonbleaching multicolor optical immunolabels.", *Proc. Natl. Acad. Sci., USA*, 97(3):996-1001(2000).
Shaida, et al., "Expression of BNIP3 correlates with hypoxia-inducible factor (HIF)-1α, HIF-2α and the androgen receptor in prostate cancer and is regulated directly by hypoxia but not androgens in cell lines", *The Prostate*, 68(3):336-343 (2008).
Shen, et al., "Enhanced and prolonged cross-presentation following endosomal escape of exogenous antigens encapsulated in biodegradable nanoparticles", *Immunol.*, 117:78-88 (2006).
Shestopalov, et al., "Multi-step synthesis of nanoparticles performed on millisecond time scale in a microfluidic droplet-based system.", *Lab on a Chip*, 4(4):316-321 (2004).
Shiow, et al., "CD69 acts downstream of interferon-alpha/beta to inhibit S1P1 and lymphocyte egress from lymphoid organs.", *Nature*, 440(7083):540-544 (2006).
Silver, et al., "Prostate-specific membrane antigen expression in normal and malignant human tissues.", *Clin. Cancer Res.*, 3(1):81-85 (1997).
Smith-Jones, et al., "In vitro characterization of radiolabeled monoclonal antibodies specific for the extracellular domain of prostate-specific membrane antigen.", *Cancer Res.*, 60(18):5237-5243 (2000).
Sondel, et al., "Preclinical and clinical development of immunocytokines.", *Curr. Opin. Investig. Drugs*, 4(6):696-700 (2003).

Song, et al., "A Microfluidic System for Controlling Reaction Networks in Time", *Angewandte Chemie—Int'l Ed.*, 42:768-772 (2003).
Spooner, et al., "A novel vascular endothelial growth factor-directed therapy that selectively activates cytotoxic prodrugs.", *Br. J. Cancer*, 88(10):1622-1630 (2003).
Stoermer, et al., "Synthesis and biological evaluation of hydroxamate-Based inhibitors of glutamate carboxypeptidase II.", *Bioorg. Med. Chem. Lett.*, 13(13):2097-2100 (2003).
Storm, et al., "Surface Modification of Nanoparticles to Oppose Uptake by the Mononuclear Phagocyte System", *Adv. Drug Deliv. Rev.*, 17:31-48 (1995).
Stroock, et al., "Chaotic mixer for microchannels.", *Science*, 295(5555):647-651 (2002).
Sutcliffe, et al., "Antibodies that react with predetermined sites on proteins", *Science*, 219:660-666 (1983).
Tang, et al., "In Vitro Gene Delivery by Degraded Polyamidoamine Dendrimers", *Bioconjugate Chem.*, 7:703-714 (1996).
Tang, et al., "Prostate targeting ligands based on N-acetylated alpha-linked acidic dipeptidase.", *Biochem. Biophys. Res. Commun.*, 307(1):8-14 (2003).
Taylor, et al., "Macrophage receptors and immune recognition.", *Annu. Rev. Immunol.*, 23:901-944 (2005).
Tindall, et al., "The Rationale for Inhibiting 5α-Reductase Isoenzymes in the Prevention and Treatment of Prostate Cancer", *The Journal of Urology*, 179(4):1235-1242 (2008).
Trindade, et al., "Nanocrystalline Semiconductors: Synthesis, Properties, and Perspectives", *Chem. Mat.*, 13(11):3843-3858 (2001).
Tsukamoto, et al., "Phosphonate and phosphinate analogues of N-acylated gamma-glutamylglutamate. potent inhibitors of glutamate carboxypeptidase II.", *Bioorg. Med. Chem. Lett.*, 12(16):2189-2192 (2002).
Uhrich, et al., "Polymeric Systems for Controlled Drug Release", *Chem. Rev.*, 99(11):3181-3198 (1999).
Unkeless, et al., "Structure and function of human and murine receptors for IgG.", *Annu. Rev. Immunol.*, 6:251-281 (1998).
Uwatoku, et al., "Application of Nanoparticle Technology for the Prevention of Restenosis After Balloon Injury in Rats," *Circ. Res.*, 92(7): e62-9 (2003).
Valentini, et al., "Association of anthracycline derivatives with DNA: a fluorescence study.", *Farmaco [Sci]*, 40:377-390 (1985).
Vallabhajosula, et al., "Radioimmunotherapy of prostate cancer in human xenografts using monoclonal antibodies specific to prostate specific membrane antigen (PSMA): studies in nude mice.", *Prostate*, 58(2):145-155 (2004).
Vascotto, et al., "Antigen presentation by B lymphocytes: how receptor signaling directs membrane trafficking.", *Curr., Opin., Immunol.*, 19(1):93-98 (2007).
Vihko, et al., "Radioimaging of Prostatic Carcinoma With Prostatic Acid Phosphatase—Specific Antibodies", *Biotechnology in Diagnostics*, 131-134 (1985).
Von Allmen, et al., "V domain of RAGE interacts with AGEs on prostate carcinoma cells", *The Prostate*, 68(7):748-758 (2008).
Von Andrian and Mempel, "Homing and cellular traffic in lymph nodes.", *Nat. Rev. Immunol.*, 3(11):867-878 (2003).
Wang, et al., "A novel biodegradable gene carrier based on polyphosphoester.", *J. Am. Chem. Soc.*, 123(38):9480-9481 (2001).
Wang, et al., "Autoantibody signatures in prostate cancer.", *N Engl J Med*, 353(12):1224-1235 (2005).
Wang, et al., "Identification of prostate specific membrane antigen (PSMA) as the target of monoclonal antibody 107-1A4 by proteinchip; array, surface-enhanced laser desorption/ionization (SELDI) technology.", *Int. J. Cancer*, 92(6):871-876 (2001).
Wang, et al., "Interactions between an anthracycline antibiotic and DNA: molecular structure of daunomycin complexed to d(CpGpTpApCpG) at 1.2-A resolution.", *Biochemistry*, 26(4):1152-1163 (1987).
Weaver, et al., "Transferrin receptor ligand-targeted toxin conjugate (Tf-CRM107) for therapy of malignant gliomas.", *J. Neurooncol.*, 65(1):3-13 (2003).
Wessels, et al., "Studies of group B streptococcal infection in mice deficient in complement component C3 or C4 demonstrate an essential role for complement in both innate and acquired immunity.", *Proc. Natl. Acad. Sci., USA*, 92(25):11490-11494 (1995).

(56) References Cited

OTHER PUBLICATIONS

Whelan, et al., "Efficient recovery of infectious vesicular stomatitis virus entirely from cDNA clones.", *Proc. Natl. Acad. Sci., USA*, 92(18):8388-8392 (1995).
Wilson, et al., "The Structure of an Antigenic Determinant in a Protein", *Cell*, 37:767-778 (1984).
Wind, et al., "An integrated confocal and magnetic resonance microscope for cellular research.", *J. Magn. Reson.*, 147(2):371-377 (2000).
Wlotzka, et al., "In vivo properties of an anti-GnRH Spiegelmer: an example of an oligonucleotide-based therapeutic substance class," *Proc. Natl. Acad. Sci. U. S. A.*, 99(13):8898-902 (2002).
Wright, et al., "Cyclophosphamide/granulocyte colony-stimulating factor causes selective mobilization of bone marrow hematopoietic stem cells into the blood after M phase of the cell cycle.", *Blood*, 97(8):2278-2285 (2001).
Wu, "Arming antibodies: prospects and challenges for immunoconjugates.", *Nat. Biotechnol.*, 23(9):1137-1146 (2005).
Wu, et al., "Immunofluorescent labeling of cancer marker Her2 and other cellular targets with semiconductor quantum dots.", *Nat. Biotechnol.*, 21(1):41-46 (2003).
Yang, "Imaging of vascular gene therapy.", *Radiology*, 228:36-249 (2003).
Yoo, et al., "In vitro and in vivo anti-tumor activities of nanoparticles based on doxorubicin-PLGA conjugates.", *J. Control. Release*, 68(3):419-431 (2000).
Yuan, et al., "siRNA Selection Server: an automated siRNA oligonucleotide prediction server.", *Nucl. Acids. Res.*, 32:W130-W134 (2004).
Zamore, et al., "RNAi: double-stranded RNA directs the ATP-dependent cleavage of mRNA at 21 to 23 nucleotide intervals.", *Cell*, 101(1):25-33 (2000).
Zauner, et al., "Polylysine-basedtransfection systems utilizing receptor-mediated delivery.", *Adv. Drug Del. Rev.*, 30:97-113 (1998).
Zhang, et al., "The proliferative effect of estradiol on human prostate stromal cells is mediated through activation of ERK", *The Prostate*, 68(5):508-516 (2008).
Zheng, et al., "Highly fluorescent, water-soluble, size-tunable gold quantum dots.", *Phys. Rev. Lett.*, 93(7):077402 (2004).
Zhou, et al., "Investigation on a novel core-coated microspheres protein delivery system.", *J. Control. Release*, 75(1-2):27-36 (2001).
Zhou, et al., "Preparation of poly(L-serine ester): a structural analog of conventional poly(L-serine)", *Macromolecules*, 23(14):3399-3406 (1990).
Zuker, "Mfold web server for nucleic acid folding and hybridization prediction", *Nuc. Acid. Res.*, 31:3406-3415 (2003).
Bies at al., "Lectin-medicated drug targeting: history and applications", *Advanced Drug Delivery Reviews*, 56:425-435 (2004).
Bocca, et al., "Phagocytic uptake of fluorescent stealth solid lipid nanoparticles", *Int. J. Pharmaceutics*, 175:185-193 (1998).
Brooking et al., "Transport of Nanoparticles Across the Rat Nasal Mucosa", *Journal of Drug Targeting*, 9(4):267.279 (2001).
Chandy et al., "Development of Poly(Lactic Acid)/Chitosan Co-Matrix Microspheres: Controlled Release of Taxol-Heparin for Preventing Restenosis", *Drug Delivery*, 8:77-86 (2001).
Chandy, et al., "5-Fluorouracil-loaded chitosan coated polylactic acid as biodegradable drug carriers for cerebral tumors", *J. Microencapsulation*, 17(5):625-638 (2000).
Cheng, et al., "Formulation of functionalized PLGA-PEG nanoparticles for in vivo targeted drug delivery", *Biomaterrials*, 28:869-875 (2007).
Coppi, et al., "Chitosan-Alginate Microparticles as a Protein Carrier", *Drug Development and Industrial Pharmacy*, 27(5):393-400 (2001).
Elvassore, et al., "Production iof Insulin-Loaded Poly(Ethylene Glycol)/Poly(/-Lactide) (PEG/PLA) Nanoparticles by Gas Antisolvent Techniques", *Journal of Pharmaceutical Sciences*, 90(10):1628-36 (2001).
Ermak and Giannasca, "Microparticle targeting to M cells", *Advanced Drug Delivery Reviews*, 34:261-283 (1998).

Fi Li Povic-Grcic et al., "Mucoadhesive chitosan-coated liposomes: characteristics and stability", *J. Microencapsulation*, 18 1:3.12 (2001).
Gaserod et al., "The enhancement of the bioadhesive properties of calcium alginate gel beads by coating with chitosan", *Intl. J. of Pharmaceutics*, 175:237-246 (1998).
Hejazi et al ., "Stomach-specific anti-H. pylon therapy. I: preparation and characterization of tetracyline-loaded chitosan microshpheres", *Intl. J. of Pharmaceutics*, 235:87-94 (2002).
Huang et al., "Microencapsulation of Chlorpheniramine Maleate-Resin Particles with Crosslinked Chitosan for Sustained Release", *Pharmaceutical Development and Technology*, 41:107-115 (1999).
Janes et al., "Chitosan nanoparticles as delivery systems for doxorubicin", *Journal of Controlled Release*, 73:255-267 (2001).
Jayasena, "Aptamers: An Emerging Class of Molecules That Rival Antibodies in Diagnostics", *Clinical Chemistry*, 45(9):1628-1650 (1999).
Kawashima, et al., "Mucoadhesive DL-Lactide/Glycolide Copolymer Nanoshperes Coated with Chitosan to Improve Oral Delivery of Elcatonin", *Pharmaceutical Development and Technology*, 5(11:77-85(2000).
Khandare, et al., "Polymer-drug conjugates: Progress in polymeric prodrugs," *Progress in Polymer Science*, 31(4): 359-397 (2006).
Kim, et al., "Target-specific cellular uptake of PLGA nanoparticles coated with poly(L-lysine)-poly(ethyleneglycol)-folate conjugate", *Langmuir*, 21(19): 8852-8857 (2005).
Lehr, "Lectin-mediated drug delivery: The second generation of bioadhesives", *J. of Controlled Release*, 65:19-29 (2000).
Lim et al., "Preparation and evaluation of the in vitro drug release properties and mucoadhesion of novel microspheres of hyaluronic acid and chitosan", *J. of Controlled Release*, 66:281-292 (2000).
Mi, et al., "Release of Indomethacin from a Novel Chitosan Microsphere Prepared by a Natrually Occurring Crosslinker: Examination of Crosslinking and Polycation-Anionic Drug Interaction", *J. of Applied Polymer Science*, 81:1700-1711 (2001).
Olivier, et al., "Drug Transport to Brain with Targeted Nanoparticles", *J. of the Am. Society of Experimental Neuro Therapeutics*, 2:108-119 (2005).
Pimentel, et al., "Peptide nanoparticles as novel immunogens: design and analysis of a prototypic severe acute respiratory syndrome vaccine", *Chemical Biology & Drug Design*, 73(1):53-61 (2009).
Ponchel, et al., "Specific and non-specific bioadhesive particulate systems for oral delivery to the gastrointestinal tract", *Advanced Drug Delivery Reviews*, 34:191-219 (1998).
Shimoda, et al., "Bioadhesive Characteristics of Chitosan Mircroshperes to the Mucosa of Rat Small Intestine", *Drug Delvelopment and Inustrial Pharmacy*, 27(6):567-576 (2001).
Simberg, et al., "Biomimetic amplification of nanoparticle homing to tumors", *Nat'l. Acad. Sic. USA*, 104(3):921-936 (2007).
Takeuchi, et al., "Enteral Absorption of Insulin in Rats from Mucoadhesive Chitosan-Coated Liposomes", *Pharmaceutical Research*, 13(6):896-901 (1996).
Takeuchi et al., "Mucoashesive Lipsomes Coated with Chitosan or Carbopol for Oral Administration of Peptide Drugs", *Proceed. Intl. Symp. Control. Rel. Blood. Mater.*, 26:988-989 (1999).
Takeuchi, et al., "Spray-Dried Lactose Composite Particles Containing an Ion Complex of Alginate-Chitosan for Desinging a Dry-Coated Tablet Having a Time-Controlled Releasing Function", *Pharmaceutical Research*, 17 (1):94-99 (2000).
Tavitian, et al., "In vivo imaging with oligonucleotides for diagnosis and drug development", *Gut, 52 Su*, I IV :40-47 (2003).
Tobio, et al "Role of PEG on the stability in digestive fluids and in vivo fate of PEG-PLA nanoparticles following oral administration", *Colloids and Surfaces B: Biointerferences*, 18:315-323 (2000).
Vila, et al., "Design of biodegradable particles for protein delivery", *Journal of Controlled Release*, 78:15-24 (2002).
Vila, et al., "PLA-PEG Nanospheres: New Carriers for Transmucosal Delivery of Proteins and Plasmid DNA", *Poly. Adv. Technol.*, 13:851-858 (2002).
Yamada, et al., "In Vitro and in Vivo Evaluation of Sustained Release Chitosan-Coat Ketoprofen Microparticles", *Yakugaku Zasshi*, 121(3):239-245 (2001).

(56) References Cited

OTHER PUBLICATIONS

Yourong, et al, "Preparation of DHAQ-loaded mPEG-PLGA-mPEG nanoparticles and evaluation of drug release behaviors in vitro/in vivo," *J. Mat. Sci.: Mat. Med.*, 17(6): 509-16 (2006).
Yuan, et al., "Intranasal immunization with chitosan/pCETP nanoparticles inhibits atherosclerosis in a rabbit model of atherosclerosis", *Vaccine, Bitterworth Scientific*, 26:29-30 (2008).
Heald, et al., "Poly(lactic acid)-poly(ethylene oxide) (PLA-PEG) nanoparticles: NMR studies of the central solidlike PLA core and the liquid PEG corona", *Langmuir*, 18:3669-3675 (2002).
Tomai, et al., "Resiquimod and other immune response modifiers as vaccine adjuvants", Expert Rev Vaccines, 6:835-847 (2007) Abstract Only.
Villa, et al., "PLA-PEG particles as nasal protein carriers: the influence of the particle size", *Int. J Pharmaceut.*, 292:43-52 (2005).
Sarkar, et al., "Ligand-DNA interaction in a nanocage of reverse micelle", Biopolymer., 83(6):675-86 (2006).
International Search Report mailed Aug. 14, 2008.
Akagi, et al., "Multifunctional conjugation of proteins on/into bio-nanoparticles prepared by amphiphilic poly(gamma-glutamic acid)", J Biomat Sci Polym Ed., 17 (8):875-92 (2006).
Akagi, et al. "Development of vaccine adjuvants using polymeric nanoparticles and their potential applications for anti-HIV vaccine", Yakugaku Zasshi, 127(2):307-17 (2007) English Abstract.
Argov-Argaman, et al., "Lactosomes: Structural and compositional classification of unique nanometer-sized protein lipid particles of human milk", J Agric Food Chem., 58:11234-42 (2010).
Avgoustakis, "Pegylated poly(lactide) and poly(lactide-co-glycolide) nanoparticles: preparation, properties and possible applications in drug delivery", Curr Drug Deliv., 1:321-33 (2004).
Chu, et al, "Aptamer:toxin conjugates that specifically target prostate tumor cells", Cancer Res., 66:5989-92 (2006).
Elamanchili, et al., "Pathogen-mimicking" nanoparticles for vaccine delivery to dendritic cells, J Cont. Rel., 30(4):378-95 (2007).
Gorelik, et al., "Scanning surface confocal microscopy for simultaneous topographical and fluorescence imaging: application to single virus-like particle entry into a cell", PNAS, 99(25):16018-23 (2002).
Hallahanm, et al., "Integrin-mediated targeting of drug delivery to irradiated tumor blood vessels", Cancer Cell, 3:63-74 (2003).
Harris, et al., "Proteolytic actuation o nanoparticle self-assembly", Angewandte Chemie, 118:3233-7 (2006).
Hennenfent, et al., "Novel formulations of taxanes: a review. Old wine in a new bottle", Ann Oncol., 17:735-49 (2005).
Jayaprakash, et al., "Design and synthesis of a PSMA inhibitor-doxorubicin conjugate for targeted prostate cancer therapy", Chem Med Chem., 1:299-302 (2006).
Kawamura, et al., "Dendritic cells that endocytosed antigen-containing IgG-liposomes elicit effective antitumor immunity", J Immunother., 29(2):165-74 (2006).
Koenig, et al., "Immunologic factors in human milk: the effects of gestational age and pasteurization", J Human Lactation, 21:439-43 (2002).
Lamalle-Bernard, et al., "Coadsorption of HIV-1 p24 and gp120 proteins to surfactant-free anionic PLA nanoparticles preserves antigenicity and immunogenicity", J Control Rel., 115(1):57-67 (2006).
Martin, et al., "Crystal structure at 2.8 A of an FcRn/heterodimeric Fc complex: mechanism of pH-dependent binding.", Mol Cell, 7:867-77 (2001).
Matsuo, et al., "Efficient generation of antigen-specific cellular immunity by vaccination with poly (gamma-glutamic acid) nanoparticles entrapping endoplasmic reticulum-targeted peptides", Biochem Biophys Res Commun., 362:1069-72 (2007).
McNeil, "Nanotechnology for the biologist", J Leukoc Biol., 78:575-94 (2005).
Moon, et al., "Engineering Nano- and microparticles to tune immunity", Adv Mater., DOI:10.1002/adma.201200446 (2012).
Oyewumi, et al., "Comparison of cell uptake, biodistribution and tumor retention of folate-coated and PEG-coated gadolinium nanoparticles in tumor-bearing mice", J Control Rel., 93:613-26 (2004).
Oyewumi, et al., "Nano-microparticles as immune adjuvants: correlating particle sizes and the resultant immune responses", Exp Rev Vaccines, 9(9):1095-1107 (2010).
Riley, et al., "Colloidal stability and drug incorporation aspects of micellar-like PLA-PEG nanoparticles", Colloids Surfaces B Biointerfaces, 16:147-59 (1999).
Riley, et al., "Physicochemical evaluation of nanoparticles assembled from Poly(lactic acid)-Poly(ethylene glycol) (PLA_PEG) block copolymers as drug delivery vehicles", Langmuir, 17:3168-74 (2001).
Shields, et al., "High resolution mapping of the binding site on human IgG1 for Fc gamma RI, Fc gamma RII, Fc gamma RIII, and FcRn and design of IgG1 variants with improved binding to the Fc gamma R", J Biolo Chem., 276(9):6591-6604 (2001).
Shim, "One target different effects: a comparison of distinct therapeutic antibodies against the same targets", Exp Mole Med., 43(10):539-49 (2011).
Suzuki, et al., "Development of effective antigen delivery carrier to dendritic cells via Fc receptor in cancer immunotherapy", Yakugaku Zasshi, 127(2):301-6 (2007). English Abstract.
Taylor, et al., "Development of a specific system for targeting protein to metallophilic macrophages", PNAS, 101(7):1963-8 (2004).
Uto, et al., "Targeting of antigen to dendritic cells with poly(gamma-glutamic acid) nanoparticles induces antigen-specific humoral and cellular immunity", J Immunology, 178 (5):2979-86 (2007).
Wakita, et al., "An Indispensable role of type-1 IFNs for Inducing CTL-mediated complete eradication of established tumor tissue by CpG-liposome co-encapsulated with model tumor antigen", Int. Immunol., 18(3):425-34 (2006).
Yu, et al., "Engineered bio-nanocapsules, the selective vector for drug delivery system", IUBMB Like, 58(1):1-6 (2006).
Adams, et al., Amphiphilic blocking copolymers for drug delivery. J. Pharm. Sci., 92(7):1343-55 (2003).
Astete and Sablio, "Synthesis and characterization of PLGA nanoparticles", J. Biomat. Sci.,-Polymer Ed., 17:247-289 (2006).
Balenga, et al., "Protective efficiency of dendrosomes as novel nano-sized adjuvants for DNA vaccination against birch pollen allergy", J Biotech., 123(3):602-14 (2006).
Barinka, et al., "Interactions between human glutamate carboxypeptidase II and urea-based inhibitors: Structural characterization", J Med. Chem.,51:7737-43 (2008).
Barinka, et al., "Structural insight into the pharmacophore pocket of human glutamate carboxypoeptidase II", J. Med Chem., 50:3267-73 (2007).
Beck, et al., "A New Long-acting Injectable Microcapsule System for the Administration of Progesterone," Fertil. & Steril., 31(5):545-55 (1979).
Benita, et al., "Characterization of Drug-Loaded Poly(d,/-lactide) Microspheres," J. Pharm. Sci. 73(12):1721-24 (1984).
Caliceti, et al. "Effective protein release from PEG/PLA nano-particles produced by compressed gas anti-solvent precipitation techniques", J of Cont. Release, 94:195-205 (2004).
Ch'Ng, et al., "Bioadhesive Polymers as Platforms for Oral Controlled Drug Delivery II: Synthesis and Evaluation of Some Swelling, Water-Insoluble Bioadhesive Polymers," J. Pharm. Sci. 74: 399-405 (1988).
Chandran, et al, "Characterization of a targeted nanoparticle functionalized with a Urea-based inhibitor of prostate-specific membrane antigen (PSMA)", Cancer Biol & Therapy, 7(4):1-9 2008).
Chen, et al., "Radiohalogenated prostate-specific membrane antigen (PSMA)-based ureas as imaging agents for prostate cancer", J Med Chem., 51(24):7933-43 (2008).
Chickering & Mathiowitz, "Bioadhesive microspheres: i. A novel electrobalance-based method to study adhesive interactions between individual microspheres and intestinal mucosa," J. Control. Release 34:251-62 (1995).
Dancey, et al., "Therapeutic Targets:MTOR an related pathways", Cancer Biol. Ther., 5(9):1065-73 (2006).

(56) References Cited

OTHER PUBLICATIONS

Duchene, et al., "Pharmaceutical and Medical Aspects of Bioadhesive Systems for Drug Administration," Drug Development &. Ind. Pharm. 14(2&3):283-31 (1988).
Ewesuedo and Ratain, "Systemically administered drugs", Drug Delivery Systems in Cancer, Humana Press, Chapter 1:3-14 (2004).
Farokhzad, et al., "Cancer nanotechnology: drug encapsulated nanoparticle-aptmer bioconjugates for targeted delivery to prostate cancer cells", 13th Eu. Cancer Conf., Oct. 30-Nov 3, Paris France (2005).
Gu, et al., "Precise engineering of targeted nanoparticles by using self-assembled biointegrated block copolymers", PNAS, 105(7):2586-91 (2008).
Gurney, et al., "Bioadhesive intraoral release systems: design, testing and analysis," Biomaterials 5:336-40 (1984).
Hamdy, et al., "Co-delivery of cancer-associated antigen and toll-like receptor 4 ligand in PLGA nanoparticles induces potent CD8+ T cell-mediated anti-tumor immunity", Vaccine, 26(39):5046-57 (2008).
Hong, et al., "Enhanced and prolonged cross-presentation following endosomal escape of exogenous antigens encapsulated in biodegradable nanoparticles", Immunol., 117(1):78-88 (2006).
Hotter, et al., "Targeting of a B7-1 (CD80) immunoglobulin G fusion protein to acute myeloid leukemia blasts increases their costimulatory activity for autologous remission T cells.", Blood, 97(10):3138-3145 (2001).
Humblet, et al. "An HPLC/mass spectrometry platform for the development of multimodality contrast agents and targeted therapeutics: prostate-specific membrane antigen small derivatives", Contrast Med. Mol, Imaging, 1:196-211 (2006).
Humblet, et al. "High-affinity near-infrared fluorescent small-molecule contras agents for in vivo imaging of prostate-specific membrane antigen", Molecular Imaging, 4:448-62 (2005).
Igaku, "Intracellular trafficking of lipid antigens and their immune recognition by the CD1 system", Exp. Med., 24(7):936-40 (2006).
Illum, "Bioadhesive Microspheres as Potential Nasal Drug Delivery System," Int'l J. Pharm. 39: 189-99 (1987).
Jiang, et al., "Preparation of PLA and PLGA nanoparticles y binary organic solvent diffusion method", J. Cent. South Univ Technol, 10(3):202-06 (2003).
Kozikowski, et al. "Design of remarkably simple, yet potent urea-based inhibitors of glutamate carboxypeptidase II (NAALADase)", J. Med Chem, 44:298-301 (2001).
Labat-Robert & Decaens, "Glycoproteines du mucus gastrique: structure, fonctions et pathologie," Pathologie Biologie 24:241 (Paris 1979).
Lee, et al. "Adaptations of Nanoscale Viruses and Other Protein Cages for Medical Applications" Nanomedicine-Nanotechnology Biology and Medicine. 2(3):137-149 (2006).
Lehr, et al., "In vitro evaluation of mucoadhesive properties of chitosan and some other natural polymers," International J. Pharmaceutics 78: 43-48 (1992).
Lehr, et al., "Intestinal transit of bioadhesive microspheres in an in situ loop in the rat—a comparative study with copolymers and blends based on poly(acrylic acid)," J. Controlled Rel. 13:51-62 (1990).
Leon-Bay, et al., "Microsphere formation and drug delivery in a series of derivatized amino acids," Winter conference of Medicinal Chemistry (Steamboat Springs, Colarodo 1995).
Maresca, et al., "A series of halogenated heterodimeric inhibitors of prostate specific membrane antigen (PSMA) as radiolabeled probes for targeting prostate cancer", J. Med Chem., 52(2):347-57 (2009).
Martinez-Pomares, et al., "Fc chimeric protein containing the cysteine-rich domain of the murine mannose receptor binds to macrophages from splenic marginal zone and lymph node subcapsular sinus and to germinal centers", J Experimental Med., 184(5):1927-37 (1996).
Mathiowitz, et al., "Morphology of polyanhydride microsphere delivery systems," Scanning Microscopy 4(2):329-340 (1990).
Mease, et al., "N-[N-[(S)-1,3-Dicarboxypropyl]carbamoyl]-4-[18F]fluorobenzyl-L-cysteine, [18F]DCFBC: a new imaging probe for prostate cancer", Clin. Cancer Res., 14(10):3036-43 (2008).
Mikos, et al., "Interaction of Polymer Microspheres with Mucin Gels as a Means of Characterizing Polymer Retention on Mucus," J. Colloid & Interface Sci. 143(2):366-73 (1991).
Misra, et al., "Production of multimeric prostrate-specific membrance antigen small-molecule radiotracers using a solid-phase 99mTc preloading strategy", J Nuclear Medicine, 48(8):1379-89 (2007).
Pomper, et al., "New developments in molecular imaging of prostate cancer", Topical Symposium on Advanced Molecular Imaging Techniques in the detection, diagnosis, therapy and follow-up of Cancer, Palazzo Barberini, Rome Dec. 6, 2005.
Pulkkinen, et al., "Three-step tumor of paclitaxel using biotinylated PLA-PEG nanoparticles and avidin-biolin technology: Formulation developing and in vitro anticancer activity", Eur. J Pharm. Biopharm., 70:66-74 (2008).
Raghuvanshi, et al., "Improved immune response from biodegradable polymer particles entrapping tetanus toxoid by use of different immunization protocol and adjuvants", Int J Pharm., 245(1-2):109-21 (2002).
Sapra, et al., "Ligan-targeted liposomal anticancer drugs", Pergamon, Progress in Lipid Research, 42:439-462 (2003).
Scawen, et al., "The Action of Proteolytic Enzymes on the Glycoprotein from Pig Gastric Mucus," Biochemical J. 163:363-68 (1977).
Smart, et al., "An in vitro investigation of mucosa-adhesive materials for use in controlled drug delivery," J. Pharm. & Pharmacol. 36:295-99 (1984).
Spiro, "Glycoproteins," Annual Review of Biochemistry 39:599-638 (Snell, ed. 1970).
Surgery Frontier, "What's new in surgery frontier", 13(3):290-3 (2006).
Sweetman, "Entry for Docetaxel", Martindale:the complete drug reference, 33rd ed., p. 534 (2002).
Tobio, et al.,"Stealth PLA-PEG nanoparticlea as protein carriera for nasal administration", Pharm. Res., 15(2):270-75 (1998).
Walter, et al., "Hydrophillic poly (DL-lactide-co-glycolide) microspheres for the delivery of DNA to human-derived macrophages and dendritic cells", J Control Release, 76(1-2):149-68 (2001).
Yamamoto, et al., „Long-circulation Poly(ethylene glycol)-poly(D,L-lactide) block copolymermicelles with modulated surace chane, J Contl Rel., 77:27-38 (2001).
Yang, et al., "Micelles formed by self-assmbling of polylactide(ethylene glycol) block copolymers in aqueous solutions", J Colloid Interfac Si., 314:470-77 (2007).

* cited by examiner

OSCILLATING CELL CULTURE BIOREACTOR

CLAIM TO PRIORITY

This application is a filing under 35 U.S.C. 371 of PCT/US2008/053411 filed with the U.S. Receiving Office of the Patent Cooperation Treaty on Feb. 8, 2008, and claims priority to and benefit of U.S. Ser. No. 60/889,046 filed Feb. 9, 2007, and where permissible are incorporated herein in their entirety.

STATEMENT REGARDING FEDERAL SPONSORED RESEARCH

This invention was made with government support under Contract No. NNJ04HC72G, awarded by the National Aeronautics and Space Administration. The government has certain rights in this invention.

FIELD OF THE INVENTION

The present invention generally relates to methods and devices for cell or tissue culture and cell or tissue culture bioreactor systems.

BACKGROUND OF THE INVENTION

Tissue-engineering holds the promise of repairing or replacing failing organs to treat illness or improve and extend life expectancy. One of the principle methods behind tissue engineering involves growth of the relevant three-dimensional (3D) organ or tissue starting from dissociated cells and 3D porous matrices, known as scaffolds. The cells attach and colonize the scaffold to produce tissue constructs (Langer, R., Vacanti, J. P. (1993) Tissue engineering. Science 260: 920-926). Bioreactors are an important tool for successful clinical implementation of tissue-engineering and regenerative medicine strategies, as bioreactors are able to reliably reproduce physiological conditions in vitro. Improved bioreactors are needed to improve engineered tissue construct size, structure, mechanical properties, cellularity, and molecular composition to more closely resemble functional native tissues, and to maintain viability of harvested cells prior to their actual transplantation One major challenge in tissue engineering that can be met by using a bioreactor is cell attachment to a 3D porous scaffold, herein referred to as 'cell seeding'. To create an autologous implant starting from a biopsy of limited size and cells of limited expansion potential, the harvested cells should be seeded onto scaffolds with the highest possible efficiency. A spatially uniform distribution of cells throughout a 3D scaffold should provide the basis for homogeneous tissue generation, but it is challenging to disperse viable cells throughout 3D scaffolds having complex and diverse architectures.

A commonly used method of cell seeding is to add concentrated cells to a scaffold in a petri dish, but this 'static seeding' method is associated with low efficiency and spatially non-uniform cell distributions. Alternatively, cells can either be added to a magnetically stirred spinner flask in which scaffolds are threaded on needles and hence fixed in place or perfused through a cartridge in which a scaffold is fixed in place. However, previously developed cell seeding devices were associated with low efficiency and spatially non-uniform cell distributions.

Subsequent to cell seeding, sufficient transport of gases, nutrients and other molecules during the culture of large tissue constructs has been a primary obstacle in the field of tissue engineering. A cell culture device should provide high rates of gas exchange (for cell types with high oxygen requirements), relatively low working volumes (for cell types that require media supplementation with costly growth factors) and controllable levels of hydrodynamic shear (for cell types that are shear-sensitive).

A related challenge in the field of regenerative medicine that can be met by using a bioreactor is to maintain the viability of harvested cells prior to the time of their actual transplantation. Harvested cells typically die or lose their specialized phenotype (de-differentiate) when cultured in conventional petri dishes or spinner flasks. Moreover, shear stress, which is absent in petri dishes and present at high levels in spinner flasks, is required to support the oxygen and nutrient transport requirements of metabolically active cells, but high levels of shear stress can induce programmed cell death (apoptosis) and/or de-differentiation.

Current cell culture bioreactors suffer from several drawbacks. For example, typical cell culture bioreactor devices require two distinct system components: one to provide gas exchange and another to provide perfusion. The requirement for two separate components renders the devices bulky and cumbersome. Additionally, existing bioreactor devices work in two distinct phases: one device is required for the cell seeding phase and a second device is required for the cell culture phase. Lastly, the majority of the existing bioreactor devices developed for cell seeding and culture are of limited use in a commercial setting, due to complexity of the required components, e.g. multi-channel peristaltic pumps, bi-directional syringe pumps or vacuum pumps combined with multiple sensors and solenoid valves.

Therefore, it is an objective of the invention to provide an integrated cell culture bioreactor suitable for cell seeding and cell culture for the production of tissue engineered constructs.

It is a further objective of the invention to provide methods for producing tissue constructs using a single, integrated bioreactor for cell seeding and cell culture.

It is a further objective of the invention to provide a cell culture bioreactor that combines effective mass transport of gases, nutrients, and regulatory molecules in the context of a single, integrated and commercially applicable device.

It is a further objective of the invention to provide a method and cell culture apparatus that can provide sufficient transport of gases, nutrients and other molecules during the culture of tissue constructs greater than 200 µm one dimension.

It is still another objective of the invention to provide an integrated cell culture bioreactor suitable for maintaining the viability of harvested cells prior to the time of their actual transplantation.

SUMMARY OF THE INVENTION

Methods and devices for cell or tissue culture on support matrices are provided which use a bioreactor having a gas permeable, closed-loop chamber for cell or tissue culture, and an oscillating means for moving the gas permeable, closed-loop chamber bidirectionally along an axis horizontal to an axis normal to the closed-loop chamber to force convection of cells and fluid within the gas permeable, closed-loop chamber. The bioreactor optionally includes inlet and outlet means. The bioreactor may include a plurality of gas permeable, closed-loop chambers for cell or tissue culture. This compact, integrated bioreactor provides high efficiency, spatially uniform seeding of cells throughout 3D porous scaffolds and produces tissue constructs through the combination of effective mass transport of gases, nutrients, and growth factors in the context of a commercially applicable device. The bioreactor can also provide a low, controllable level of shear stress to meet the metabolic requirements of shear-sensitive cells without compromising their viability.

The methods of producing a tissue construct include the steps of obtaining a tissue biopsy from a patient, expanding cells of the biopsy in vitro, and culturing the cells in the bioreactors containing a scaffold to produce a tissue construct. In one embodiment, "perfusion seeding and culture", the method of producing a tissue construct involves inoculating a cells and culture media into a gas permeable, closed loop chamber containing a porous three dimensional ("3D") scaffold, oscillating this chamber bidirectionally along an axis horizontal to an axis normal to the closed-loop chamber to force convection of the cell suspension through the scaffold, and culturing the cell-scaffold composition under physiologic conditions to produce a tissue construct.

In another embodiment, "perfusion culture after seeding", the method of producing a tissue construct includes the steps of loading a cell-hydrogel composition and culture media into a gas permeable, closed-loop chamber, sealing the gas permeable, closed-loop chamber, oscillating it bidirectionally along an axis horizontal to an axis normal to the closed-loop chamber to force convection of the culture media, and culturing the cell-hydrogel composition under physiological conditions to produce a tissue construct. In another embodiment, the method of producing a tissue construct includes the steps of loading a cell-hydrogel composition in combination with a 3D porous scaffold and culture media into a gas permeable, closed-loop chamber, sealing the gas permeable, closed-loop chamber, oscillating it bidirectionally along an axis horizontal to an axis normal to the closed-loop chamber to force convection of the culture media, and culturing the cell-hydrogel-scaffold composition under physiological conditions to produce a tissue construct.

Another embodiment, "culture of adherent cells or cells in suspension" provides a method of maintaining cell viability and includes the steps of inoculating cells and culture media into a closed-loop chamber not containing a scaffold, and oscillating the gas permeable, closed-loop chamber bidirectionally along an axis horizontal to an axis normal to the closed-loop chamber to force convection of the cells and culture media to maintain cell viability.

Still another embodiment provides a bioreactor system that is an integrated, system. In another embodiment, the bioreactor system includes modules for ease of scale-up and automation.

Another embodiment provides methods of treatment using tissue constructs produced according to the disclosed methods.

BRIEF DESCRIPTION OF THE DRAWINGS

FIG. 3A is a graph of DNA (μg/construct) of 4-day constructs and FIG. 3B is the cross-sectional thicknesses (mm/construct) of 14-day constructs, comparing results after seeding chondrocytes onto 3-dimensional scaffolds in the oscillating perfused bioreactor ("OPB"), static culture ("ST"), or spinner flask culture ("SF"). Data are Avg.±SD of 3-4 measurements; * significant difference between OPB and ST; ** significant difference due to seeding and culture method.

FIG. 4A, cell viability (MTT assay), FIG. 4B, apoptosis (TUNEL positive cells, %); FIGS. 4C and 4D, cardiac troponin-I and connexin-43, respectively (cardiac marker proteins, % native heart); FIG. 4E, total protein (mg/construct); FIG. 4F, contractile amplitude (% area change); FIG. 4G, excitation threshold (volts). Data are Avg.±SEM of 3-6 measurements for A-E or 12-28 measurements for F-G; * significantly different from ST CTL; † significantly different from ST+IGF; ‡ significantly different from OPB CTL.

DETAILED DESCRIPTION OF THE INVENTION

I. Cell Culture Bioreactors

One embodiment of an oscillatory cell culture bioreactor system provides flow of cell suspensions and/or culture media directly through a porous 3D scaffold (during cell seeding) and a 3D construct (during subsequent cultivation) within a gas-permeable closed-loop tube. The bioreactor is designed to exploit the principles of gas transport and mass transport during the processes of cell culture and cell seeding of 3D scaffolds and in vitro culture of 3D tissue engineered constructs. The bioreactor can also be used with cells in the absence of a scaffold, e.g., to maintain the viability of dissociated cells in suspension. In certain embodiments, the bioreactor is simple, modular, and flexible, and the component parts are easy to assemble, operate and inexpensive. Chamber volume can be very low, but can also be easily scaled up for commercial uses. The bioreactors are well suited to work with different biological specimens (including in particular cells with high oxygen requirement and/or shear sensitivity), different scaffold structures and dimensions, and combinations thereof.

Bioreactors based on the disclosed design should increase the efficacy of mass transport. Since the bioreactors can be used without any set-up modification to move from the seeding to the culturing phase, these bioreactors are expected to increase reliability, reduce the risk of contamination, reduce sample loss, and reduce costs.

A. Closed-Loop Chamber

Figure 1:
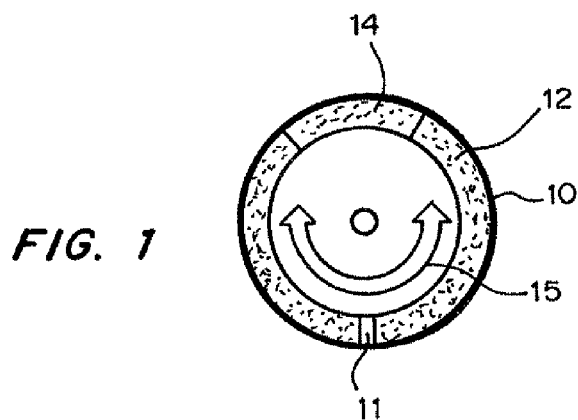
FIG. 1 is a front, cross-sectional view of one embodiment of the disclosed cell culture bioreactor.

FIG. 1 shows a representative bioreactor that includes a closed-loop chamber (10) which contains the cells to be cultured or the tissue construct to be cultured. In one embodiment of the disclosed method and apparatus, relatively small and inexpensive silicone rubber closed-loop chambers may be used to grow prokaryotic or eukaryotic, preferably mammalian cells with growth kinetics and final saturation densities that are similar to or higher than those observed using conventional culture systems. The silicone rubber closed-loop chambers may produce cell and tissue growth rates higher than the growth rates obtained using conventional methods of cell culture including static, mixed, and magnetically stirred flasks.

The closed-loop chamber (10) is formed at least in part from a gas permeable material, preferably a highly gas permeable material, to allow efficient gas exchange during the cell seeding/culturing process. Efficient gas exchange by a gas permeable material is defined as that required to maintain equilibrated in the cell culture medium within the closed-loop chamber dissolved gas concentrations that are physiological for the cells cultured therein (e.g., for heart cells, dissolved oxygen preferred >75 mm Hg, more preferred >80 mm Hg, most preferred, >85 mm Hg. Suitable gas permeable materials include, but are not limited to, gas-permeable materials including hydrophobic polymer materials such as silicone and polydimethylsiloxane ("PDMS"). Silicone rubber and other suitable gas permeable polymers provide means for the facile transport of oxygen and/or other gases into or away from a culture. Silicone rubber has a relatively high permeability to $O_2$ and $CO_2$ when compared to other known polymers. For example, the permeability (in $[cm^3][cm]/[cm^2][S][cm\ Hg]\times10^{13}$) of silicone rubber to $O_2$ and $CO_2$ is 367 and 2430, respectively. In comparison, the permeability of polystyrene film is 2.0 and 7.9, respectively. The permeability of polyethylene is comparable to polystyrene. Thus, silicone rubber has over 100 times the $O_2$ permeability of polystyrene, polyethylene, or virtually any other polymer. Furthermore, in addition to being permeable to oxygen, carbon dioxide, nitrogen, and other low molecular weight gases, silicone rubber may also be permeable to other volatile molecules, such as ethylene oxide (ETO). Therefore, permeability of silicone rubber and other suitable polymers to unwanted reagents such as ETO may allow their non-invasive removal in some embodiments.

The closed-loop chamber can be partially or completely formed of optically translucent or clear material. The closed-loop chamber (10) has a holder (11) for securing a scaffold (32), which may be a hydrogel and/or fibrous, sponge-like, mesh, non-woven mesh, woven fabric, foam, decellularized tissue or capillary with or without additional support or another form. Within the holder (11), the scaffold (32) may be secured directly to the wall of the closed-loop chamber (10) or placed within a means for retaining the scaffold (32) such as a porous bag or frame secured to the wall of the closed-loop chamber (10). The motion (15) forces the fluid and cells and gases through the entire thickness of the scaffold. In a preferred embodiment, scaffold (32) is more than 200 micrometers in diameter, so that the fluids must transport nutrients and gases over a distance greater than 200 micrometers. This is significant because nutrients and gases normally do not diffuse more than a distance of 100 micrometers within a tissue, and, absent vascular flow, the cells die or fail to attach and proliferate at the farther distances from the exterior surfaces of the scaffold or tissue construct.

Figure 2:
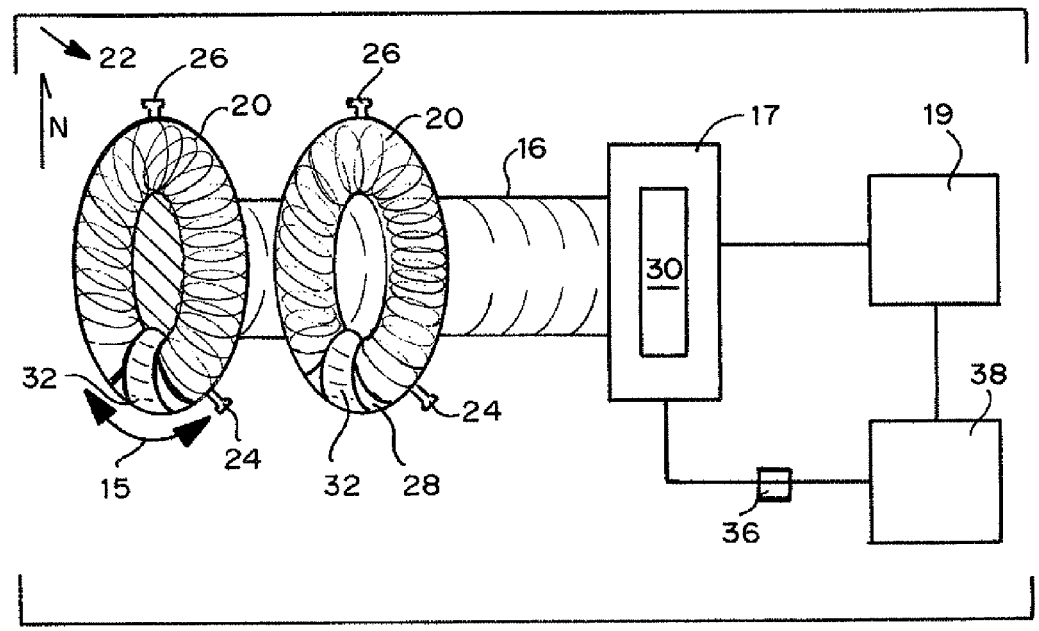
FIG. 2 is a side, perspective view of a diagram of another embodiment of the bioreactor.

One embodiment provides one or more toroidal closed-loop chamber(s) (20) as shown in FIG. 2. The toroidal closed-loop chamber is formed, for example, by fusing the ends of a tube, preferably a silicone rubber tube or other gas permeable material. N in FIG. 2 indicates the normal axis.

In one embodiment, a fluid (12), with or without cells, is added to closed-loop chamber (10 or 20) such that all or most of the air is displaced (i.e., with or without an enclosed air bubble (14)). Typically, the fluid is conventional cell culture fluid containing nutrients and growth factors sufficient to culture cells or tissue constructs. Other types of fluids include, but are not limited to, growth media containing regulatory molecules such as paracrine factors, micro or nanoparticles, quantum dots, or other agents for regulating, detecting and/or monitoring cellular activity or chemical species.

The gas permeable, closed-loop chambers can be of any size or dimension. A single bioreactor system can contain multiple chambers that have different capacities. The chambers can be partially or completely filled with fluid. In certain embodiments, the interior surfaces of the close-loop chambers are coated with material to promote or prevent cell attachment such as the silicone-based spray-coating SIGMA-COTE™.

In other embodiments, the closed-loop chamber optionally includes a chamber occlusion system, for example a roller like that used to propel fluid in a standard peristaltic pump.

Another embodiment provides closed-loop chambers configured with an outlet to be used with/without a 10-μm pore cut-off membrane to sample media without/with cells.

Referring to FIG. 2, another embodiment provides an oscillating cell culture bioreactor system within housing (22). Housing (22) provides a controlled environment for cell or tissue culture, for example a humidified 37° C., 5% $CO_2$ incubator. The conditions of the controlled environment can be adjusted to optimize the culture conditions for different cells or tissue types.

One or more closed-loop chambers (20) are removably attached to shaft (16). Shaft (16) is attached to motor (17) that provides an oscillatory movement to the closed-loop chambers (20). Arrow (15) indicates one embodiment of the direction of the applied oscillating movement. Movement of the closed-loop chamber (20) induces relative motion of the closed-loop/scaffold/construct with respect to the fluid (12). In the case where the fluid is a cell suspension, cells will come into contact with the scaffold and eventually adhere to the scaffold. The fluid containing the cells can partially or completely penetrate the porous scaffold. Gas exchange (i.e., of oxygen and carbon dioxide) occurs from the environment through gas permeable walls of closed-loop chamber (20) and into the fluid (12) as required for preserving viability of metabolically active cells or tissue constructs. Controller (19) controls motor (17) to provide adjustable levels of oscillating motion to closed-loop chamber (20) and thereby achieve mass transport while also controlling the level of fluid dynamic shear occurring inside closed-loop chamber (20) for example, to preserve viability of shear-sensitive cells and also enhance their differentiation.

The oscillatory cell culture bioreactor can be easily custom-modified to match specific fluids and biological specimens for different tissue engineering applications with respect to the chamber (i.e., section, material, capacity, filling, gas permeability, optical transparency, presence and location of inlets (24)/outlets (26), sensors (25), and actuators (30), the scaffold (32) (i.e., material, structure, geometry and orientation), the type of motion (i.e., rotational, non-oscillatory, oscillatory) and its characteristics (i.e., speed, arc of oscillatory motion) and the types of fluid flow (i.e., laminar, turbulent, non-turbulent). It will be appreciated that the inlets (24) or outlets (26) can be positioned anywhere along closed-loop chamber (10 or 20), For example, outlet (26) can be positioned on the lower half of closed-loop chamber (10 or 20) similar to inlet (24).

In one embodiment of the oscillatory cell culture bioreactor, a toroidal chamber (20) was constituted by silicone tubing within which a scaffold holder (11) was molded from poly (dimethyl siloxane)(PDMS). In certain embodiments, the scaffold holder (11) is optically clear to permit visual inspection of the scaffold/tissue construct. Scaffold holder (11) can be configured to receive a scaffold (32) for culturing tissue constructs and can be formed from a variety of materials and include sensors (28) or actuators (30) suitable for the type of cell or tissue construct to be cultured.

Oscillatory motion was achieved by an electrical motor (17) turning shaft (16) where the inversion of the turning direction (15) (i.e., oscillation) was obtained and controlled by either eccentric cam rotation or a simple control circuit with micro-switches (36). The oscillatory motion can create laminar, non-turbulent motion or turbulent motion depending on the speed and angle of motion. Up to sixteen individual closed-loop toroidal chambers (20), each containing a single scaffold (32), were attached to a single shaft (16) via discs of appropriate diameter and moved in unison with the shaft. It will be appreciated that the number of closed-loop chambers can be varied, for example, from 1 to 24, preferably 5 to 16, more preferably 8-16. Oscillatory motion of the chamber forced convection of the cell suspension and culture media directly through the scaffold (32). Convective flow can be achieved either by trapping a small air bubble (14) at the top of the closed-loop chamber (20) or by using a minimally occlusive roller (not shown) to compress the tubing at the top of closed-loop chamber (20). The bioreactor system is operably connected to power supply (38).

Scale-up of the disclosed system can be easily achieved for this modular system, e.g., by stacking chambers on a single shaft of an oscillatory base; chambers with different characteristics can be stacked on the same shaft.

In one embodiment, the bioreactor system provides sixteen individual cell culture chambers, allowing one or more cell types from one or more different patients and/or culture conditions to be separately cultured within a single culturing routine, as may be required for autologous cell therapies for different patients (i.e., cells from different patients must be individually cultured, to avoid cross contamination). For example, one closed-loop chamber can be culturing cardiac mesenchymal cells, whereas another closed-loop chamber attached to the same device as shown in FIG. 2 can be culturing skeletal muscle cells from the same patient or from another patient.

In one embodiment controller (19) is a processor, for example a conventional computer. Controller (19) can be programmed to monitor culture conditions for example via input from sensors (28) and automatically vary conditions such as temperature, humidity, pH, concentrations of dissolved $O_2$ and $CO_2$, and oscillating movement including speed, arc rotation, and direction. Controller (19) is operably connected to motor (17) and power supply (38). Sensors (28) can be designed to monitor temperature, humidity, pH, concentrations of dissolved $O_2$ and $CO_2$, glucose, etc. The controller can be communicatively linked to each individual closed-loop chamber to adjust each chamber independently. Alternatively, the controller can be communicatively linked to each closed-loop chamber so that the conditions of all of the closed-loop chambers are altered uniformly.

B. Scaffold Materials

The gas permeable, closed-loop chamber can contain one or more scaffolds. The scaffold can be made of synthetic and natural polymers capable of forming a three dimensional, porous platform. Preferred polymers are biodegradable. Suitable synthetic polymers include, but are not limited to aliphatic polyesters such as polyglycolic acid (PGA), polylactic acid (PLLA), their copolymers (e.g., PLGA), polyp-dioxanone), copolymers of trimethylene carbonate and glycolide, poly(3-hydroxybutyrate), poly(3-hydroxyvalerate), poly-ε- caprolactone (PCL), poly(valcrolactone), poly(tartronic acid), poly(β-malonic acid), poly(propylene fumarates), polyanhydrides, polyorthoesters, polyurethanes diiscoyanates such as lysine diisocyanate (LDI) (2,6-diisocyanatohexanoate) and other aliphatic diisocyanates like hexamethylene diisocyanate (HDI), polyphosphazenes (P. A. Gunatillake and Raju Adhikari (2003) Eur. Cells Mater. 5:1-16), polyhydroxyalkanoates, poly(glycerol-sebacate), and xylitol-based polymers (J. P. Bruggeman et al. (Adv Mater, 2008).

In other embodiments, the polymers can be biodegradable, shape-memory polymers (A. Lendlein and R. Langer (2002) Science 296(5573):1673-1676. Additional polymers for use in the disclosed methods and devices can be found in R. A. Pethric et al. (eds) Polymer Yearbook 16, Overseas Publishers Assoc. Singapore (1999) and S. K. Mallapragada and B. Narasimhan (eds) Handbook of Biodegradable Polymeric Materials and Their Applications, American Scientific Publishers (2005), and R. Lanza, R. Langer, and J. Vacanti (eds) Principles of Tissue Engineering, $3^{rd}$ Edition (2007).

Natural polymers include but are not limited to protein or carbohydrate polymers such as collagen or gelatin and naturally occurring polymers made by recombinant DNA technology. In other embodiments, the scaffold can be formed using ceramic composites such as hydroxyapatite, tricalcium phosphate or metal meshes and foams.

One embodiment provides scaffolds formed from live or decellularized tissues, as in H. C. Ott et al., Nature Medicine (2008), and naturally occurring or semi-synthetic materials such as hyaluronan benzyl ester, HYAFF-11® (Fidia Advanced Biopolymers). Additional suitable scaffolds are those as described in U.S. Pat. No. 5,770,417 to Langer et al. and U.S. Pat. No. 6,962,814 to Mitchell et al.

One embodiment includes scaffolds having paracrine factors such as growth factors, cytokines, morphogens, cell signaling agents, nucleic acid fragments or combinations thereof releasably attached or associated with the scaffold matrix. The paracrine agents can be controllably released from the scaffold by the application of a releasing agent. The degree of release can be further controlled by the time and amount of releasing agent applied. Representative releasing agents are chemical agents or peptide agents, for example an enzyme such as an esterase. In other embodiments, the bioactive factor freely diffuses out of the scaffold. In still other embodiments, the bioactive factors are attached to the scaffold to form a gradient. Gradients of paracrine factors can be used to help direct the formation of specific tissues. Suitable growth factors include, but are not limited to, epidermal growth factor (EGF), fibroblast growth factor (FGF), hepatocyte growth factor (HOF), platelet-derived growth factor (PDGF), vascular endothelial cell growth factor (VEGF), and insulin-like growth factor (IGF). A morphogen is a substance governing the pattern of tissue development and, in particular, the positions of the various specialized cell types within a tissue. Some growth factors are also morphogens. Morphogens include bone morphogenic proteins (BMP), decapentaplegic/transforming growth factor beta, hedgehog/sonic hedgehog, wingless/Wnt, epidermal growth factor, and fibroblast growth factor, and biologically active fragments thereof.

Scaffolds or matrices can be produced using known techniques, including, but not limited to, laser microablation, free form fabrication, phase-change jet printing, 3D Plotter, Fused Deposition Modeling (FDM), Stereolithography (SLA), Three Dimensional Printing (3DP), freeze drying, solution casting, emulsion freeze drying, melt molding, phase separation, fiber meshes/fiber bonding, gas foaming, and solvent-casting particulate-leaching or a combination thereof (P. A. Gunatillake and R. Adhikari (2003) Eur. Cells Mater. 5:1-16)

(S. J. Hollister (2005) Nature Materials 4: 518-524), The size and shape of the scaffold can be varied to optimize culture of specific cells and tissue constructs.

C. Cells

Suitable cells for use in the disclosed methods and apparatus include prokaryotic and eukaryotic cells, preferably mammalian cells. Representative cells include mammalian, preferably human, cells, embryonic or adult stem cells; pluripotent or totipotent cells obtained from placenta, cord blood, adipose tissue, neural tissue, muscle tissue, cardiac tissue, parenchymal tissues, epidermal tissue, or bone marrow;, or somatic cells optionally corresponding to a tissue or organ to be treated. The cells can be derived from mesoderm, endoderm, or ectoderm. Representative cells include mesenchymal cells, especially fibroblasts, interstitial cells, endothelial cells, smooth or skeletal muscle cells, heart cells, myocytes (muscle cells), chrondocytes, adipocytes, fibromyoblasts, and ectodermal cells, including ductile and skin cells, hepatocytes, Islet cells, cells present in the intestine and other parenchymal cells, osteoblasts and other cells forming bone or cartilage, bone marrow cells and blood cells. Cells genetically engineered to avoid the need for immunosuppression in a host receiving the tissue construct may also be used.

A population of cells to be cultured can be a single type of cell, cells from a single type of tissue (for example a population of cardiac cells), or a combination of different types of cells (for example endothelial cells in combination with cardiac myocytes). The cells can be autologous, heterologous, allogenic, xenogenic, or a combination thereof.

Suitable cells also include recombinant cells that express one or more heterologous nucleic acids. The heterologous nucleic acid can express a protein involved in wound healing or tissue regeneration, for example an extracellular matrix protein, matrix metalloprotease or GAG synthase, or a fusion protein thereof. Alternatively, the cell can be genetically engineered to secrete paracrine factors including, but not limited to growth factors such as fibroblast growth factor, hepatocyte growth factor, platelet-derived growth factor, vascular endothelial cell growth factor, and insulin-like growth factor, bone morphogenic proteins and combinations thereof. The cells can also be engineered to express inhibitors of complement or inflammation, such as CD46 or CD59. Methods and protocols for producing recombinant cells are known in the art.

In some embodiments, cells are obtained by biopsy and dissociated using standard techniques, such as digestion with a collagenase, trypsin or other protease solution. Cells can be easily obtained through a biopsy anywhere in the body, for example, skeletal muscle biopsies can be obtained easily from the arm, forearm, or lower extremities, smooth muscle can be obtained from the area adjacent the subcutaneous tissue throughout the body, and bone marrow can be obtained from the iliac crest. The biopsy can be readily obtained with the use of a biopsy needle, a rapid action needle which makes the procedure extremely simple and almost painless. Cells may also be procured from, for example, cardiac tissue, blood vessels, blood, such as umbilical cord blood or adult blood, valves and discarded tissues, such as placenta and tissue obtained during orthopaedic, reconstructive, aesthetic or cosmetic surgical procedures.

For example, the dermal layer of a skin biopsy can be digested with collagenase or other proteases. After the digestion of the dermal fragments, mesenchymal cells can be harvested following centrifugation and expanded in cell culture media. Alternatively, dermal fibroblasts or adventitial fibroblasts may be used. Fibroblasts are easily available, and they are the primary collagen secreting cells in connective tissues. Dermal fibroblasts are typically harvested from normal adult skin specimens removed during reductive breast surgery, or from neonatal foreskin.

The cells, which may or may not be immobilized on or entrapped in hydrogels, microcarriers or particles including for example nanoparticles, can be introduced into the cell culture media (fluid) within the bioreactor.

II. Applications of the Bioreactors

The oscillating cell culture bioreactor can be used to culture cell populations, i.e., to maintain their viability or expand their quantity, and/or to produce tissue constructs from a suspension of cells or tissue sampled from one or more patients. The cells or tissue constructs produced using the disclosed methods and devices can be used to treat wounds, repair, restore, or replace damaged or diseased tissues or organs in a patient, for example a human. Additionally, the tissue constructs can be used in transplant procedures to replace tissues or organs or parts thereof in a patient in need of such treatment, including use of the cells within the tissue construct as sources of proteins or other products expressed by the cells, or by genes incorporated into the cells by genetic engineering. Particular embodiments provide methods for producing cardiac tissue, cartilage, bone, muscle, and skin tissue. The tissue constructs can have single or multiple layers and can be formed of the same type of cells or multiple types of cells.

The bioreactor system is useful for the mass production of cell-based, tissue engineered constructs for the repair of damaged or defective tissues, according to the tissue engineering approach wherein cells obtained by biopsy are expanded in vitro, cultured on a 3D biomaterial scaffold, and then implanted as an autograft. Accordingly, one embodiment provides a method including the steps of obtaining a sample of cells from a patient, preferably a human, expanding the sample of cells in vitro and/or culturing the cells in the bioreactor system to produce a tissue construct, and implanting the tissue construct in the same or another patient. Methods of surgical implantation are known in the art, and one of ordinary skill in the art of tissue engineering and/or medicine could readily implant the produced tissue construct into a patient.

The bioreactor devices can, be used for cell culture in at least three configurations: (1) for perfusion seeding and culture, i.e., by addition of a cell suspension into a closed chamber containing a scaffold fixed within a holder, (2) for perfusion culture after cell seeding, i.e., by addition of a previously cell seeded construct or by addition of a cell-hydrogel mix directly onto a scaffold, within a holder prior to closing and operating the chamber, and (3) for maintaining the viability of adherent cells or cells in suspension culture, i.e., by adding cell suspensions to a chamber that does not contain any biomaterial scaffold. In the first configuration, significant increases in construct cellularity, thickness, and staining for extracellular matrix demonstrated enhanced cartilage tissue regeneration in the oscillatory cell culture bioreactor.

In the second configuration, significant increases in cardiomyocyte viability, differentiation, and contractility demonstrated enhanced cardiac tissue regeneration in the oscillatory cell culture bioreactor. In the third configuration, suspended heart cells remained viable for 8 days in vitro.

A. Perfusion Seeding and Culture

One embodiment provides a method for producing a tissue construct in which a cell suspension is added into a gas permeable, closed-loop chamber optionally containing a scaffold removably attached to a holder. The method includes introduction of a cell suspension into the closed-loop system by simple injection using a syringe, for example, into a receiving means or inlet. Injection significantly reduces the risk of contamination and facilitates subsequent selective addition/sampling of products (for example, cells, paracrine factors or media). Media, paracrine factors, and pharmacological agents, as well as any other fluid or suspension, can be added through the inlet. Excess media can be drained though the outlet.

The method includes oscillating the closed-loop chamber to force convection of the cell suspension and culture media through the scaffold for example by trapping a small air bubble at the top of the closed-loop chamber or by using a minimally occlusive roller to compress the tubing at the top of closed-loop chamber. The closed-loop chamber can be oscillated by rotating the chamber about the axis parallel to shaft. The angle of rotation is typically less than 360°, preferably less than 300°, more preferably less than 240°, or most preferably 180° in one direction followed by a substantially equivalent rotation in the opposite direction. The speed of the oscillating motion can be adjusted, alone or in combination, with the angle of rotation sufficient to force convection of the cell suspension and culture media through scaffold. Forcing the cells through the scaffold is the "seeding" step of this method. As the cells are moved through the scaffold, a number of the cells will attach to the scaffold and begin to form a tissue construct. Additional cells can attach to the scaffold and to cells attached to the scaffold to form tissue.

The method further provides convective flow of the media through the construct during its culture in the closed-loop chamber. Covective flow of media through the construct is the "perfusion culture" step of this method.

The method further provides gas exchange to the media within the closed-loop chamber during both the seeding and perfusion culture steps. Typically, the closed-loop chamber is maintained in a controlled environment so that gas exchange occurs through the gas permeable walls of the closed-loop chamber. In particular, oxygen passes from the controlled environment into the closed-loop chamber in amounts sufficient to thoroughly saturate the fluid within which the growing tissue construct is immersed. In certain embodiments, the growing tissue construct is sufficiently oxygenated to produce tissue constructs having at least one dimension greater than 200 µm.

B. Perfusion Culture after Cell Seeding

Another embodiment provides a method for producing a tissue construct by oscillating a closed-loop chamber containing a previously cell seeded construct or a scaffold to which a cell-hydrogel mixture has been added. The scaffold is typically removably attached to a holder, and the holder is fixed to the closed-loop chamber. The cell-hydrogel suspension can then be entrapped within a porous scaffold by pipetting the suspension directly onto the scaffold prior to closing the toroidal chamber to localize cell delivery to the scaffold. In one embodiment, the holder is injection molded to fit into the toroidal chamber prior to closure. The toroidal chamber can be closed using conventional methods, for example, by an adhesive, thermal fusion, a clip or press-fit.

Representative hydrogels include, but are not limited to, MATRIGEL™. MATRIGEL™ is the trade name for a gelatinous protein mixture secreted by mouse tumor cells and marketed by BD Biosciences. Other suitable hydrogels are fibrin, collagen, and self-assembling peptides, such as PURAMATRIX™ marketed by 3DM™. Other suitable hydrogels are those formed from poly(hyaluronic acid), poly(sodium alginate), poly(N-isopropyl acrylamide), and poly(anhydride), poly(ethylene glycol), or combinations thereof. In certain embodiments, the hydrogels are biodegradable.

C. Culture of Adherent Cells or Cells in Suspension

Another embodiment provides cells or other biological specimens cultured in a closed-loop chamber without a scaffold, in order to maintain the viability of these cells in prolonged culture. In this method, the cells are added to the closed-loop chamber, eventually adequately coated to induce/prevent cell attachment, containing cell culture media. Typically, the cells are added by injection into the closed-loop chamber through an inlet. The closed-loop chamber is oscillated as described above to provide convection flow of the culture medium and, if necessary, to force the convection of cells off of the bottom of the chamber and maintain the cells in suspension.

D. Methods of Treatment

The cells and tissue constructs produced according the disclosed methods can be used to treat a variety of pathologies. For example, the tissue constructs can be used to treat a wound or damaged tissue of a patient. The damaged tissue can be the result of trauma, genetic defect, surgical procedure, myocardial infarction, atherosclerosis, inflammation, auto immune disease, aneurysm or congenital birth defect. In certain embodiments, the tissue constructs can be used in cosmetic procedures. In a preferred embodiment, the tissue constructs can be used to augment, fortify or support a patient's tissues.

The tissue constructs produced according to the methods disclosed herein can also be used as grafts and transplants in patients in need thereof. The tissue constructs can be formed autologous, allogenic, or xenogenic. For example, the tissue constructs can be used to treat burn victims or patients with cartilage defects by replacing damaged skin or damaged or missing cartilage in a joint.

In still another embodiment, the tissue constructs can be used to replace part or all of a defective organ for example, the heart, skin, liver, kidney, pancreas, eye, or component of the nervous system.

The methods and compositions described herein will be further understood by reference to the following non-limiting examples.

EXAMPLES

Example 1

Perfusion Seeding and Culture

Materials and Methods:

Cells harvested from bovine calf cartilage were cultured on 3D non-woven fibrous scaffolds by perfusion seeding and culture in the oscillating perfused bioreactor (OPB). The two control groups were otherwise identical constructs seeded and cultured either in spinner flasks (SF) and static petri dishes (ST). The DNA content of constructs sampled on day 4 was quantified to provide an index of cell seeding efficiency. Cross-sectional thickness of constructs sampled on day 14 was quantified to provide an index of construct growth. Cell morphology and extracelluar matrix deposition in 14-day constructs were assessed by safranin-O staining for glycosaminoglycans (GAG).

Figure 3A:
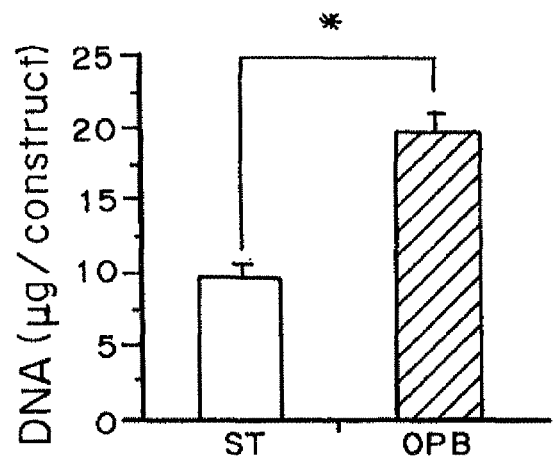
FIGS. 3A and 3B are graphs demonstrating efficacy of perfusion seeding and culture in the oscillating perfused bioreactor.
Figure 3B:
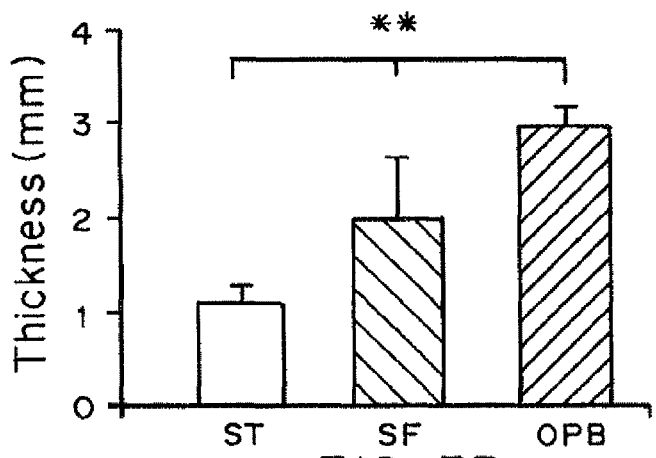

Results and Discussion:

The DNA content of 4-day constructs from the OPB group was significantly higher than the ST group, indicating that the OPB enhanced cell seeding efficiency (FIG. 3A). Cross-sectional thickness of 14-day constructs was significantly affected by the method of seeding and culture, and was highest in the OPB group, indicating the bioreactor enhanced the growth of engineered cartilage (FIG. 3B). The 14-day constructs from the ST group resembled immature cartilage consisting of small round cells and low intensity matrix staining for GAG, a key extracellular matrix component of articular cartilage, whereas those from the OPB group resembled more mature cartilage consisting of round-to-oval chondrocytes in lacunar spaces and intense, spatially homogenous matrix staining for GAG. The 14-day constructs from the SF group exhibited non-homogenous cell and tissue morphologies. Increased cellularity, thickness, and intensity of staining for glycosaminoglycans suggests that perfusion seeding and culture in the oscillating perfused bioreactor enhanced cartilage tissue regeneration.

Example 2

Perfusion Culture after Seeding

Materials and Methods:

Cells harvested from neonatal rat hearts were seeded on 3D porous solid scaffolds by entrapment in MATRIGEL® and then cultured for 8-days statically (ST) or in the oscillating perfused bioreactor (OPB) in either control (CTL) or IGF-supplemented (+IGF) media, Cell viability was quantified by the 3-(4,5-dimethylthiazol-2-yl)-2,5-diphenyl tetrazolium bromide (MTT) assay. Apoptosis was quantified by the terminal deoxynucleotidyl tranferase (TdT)-mediated dUTP nick end labeling (TUNEL) assay. Amounts of cardiac troponin-I (Tn-I) and connexin-43 were assessed by Western blot, and total protein content was quantified by a commercial kit. Contractile amplitude was assessed as percent area change during a contractile cycle by computer based image analysis. Excitation threshold (ET) was assessed by placing constructs between a pair of electrodes to which pacing stimuli were applied at 1 Hz; the voltage at which each impulse was followed by a contractile tissue response defined as the ET. Cell morphology was evaluated by immunohistochemical staining for cardiac Tn-I.

Figure 4A:
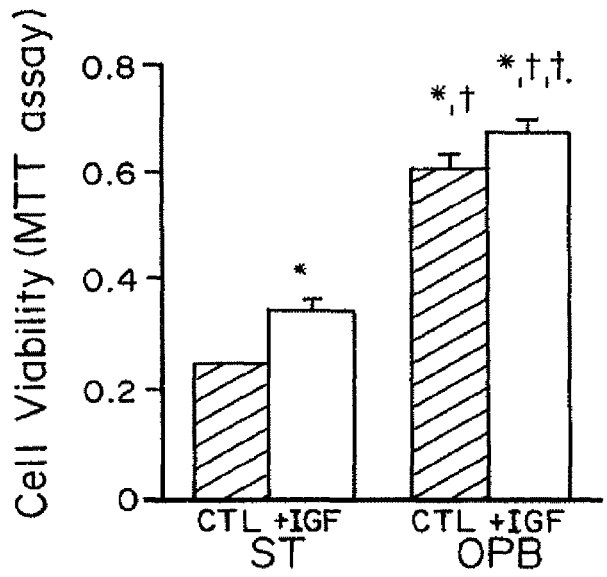
FIGS. 4A-4G are graphs comparing cell viability and tissue regeneration after 8 days of static (ST) or oscillating perfused bioreactor (OPB) culture of cardiomyocytes entrapped within porous 3D scaffolds using Matrigel, in control (CTL) or JOF supplemented (+IGF) media.
Figure 4B:
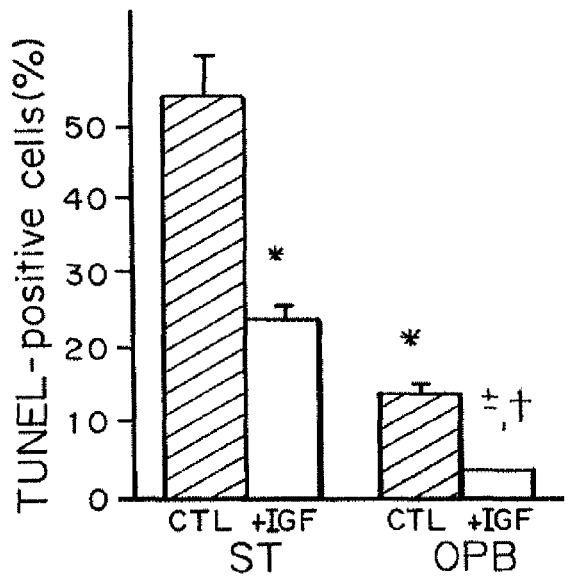
Figure 4C:
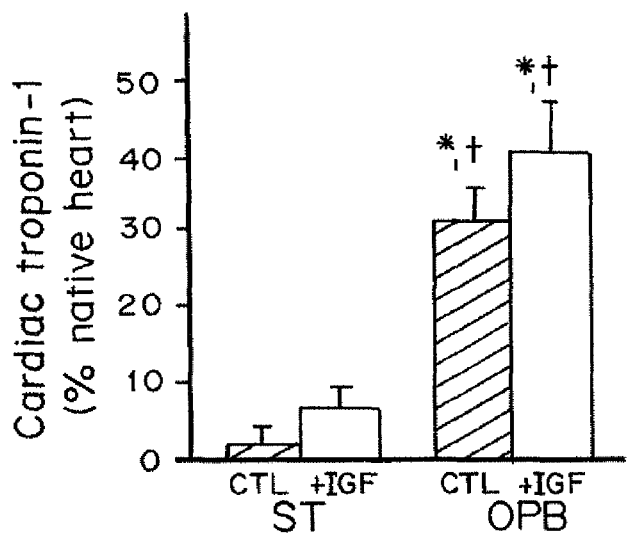
Figure 4D:
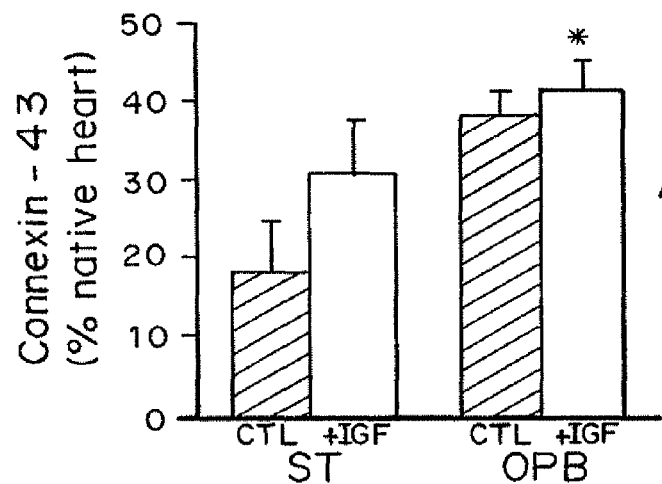
Figure 4E:
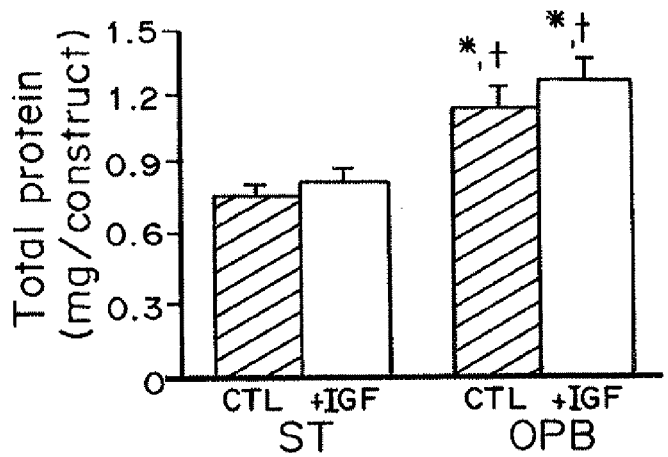
Figure 4F:
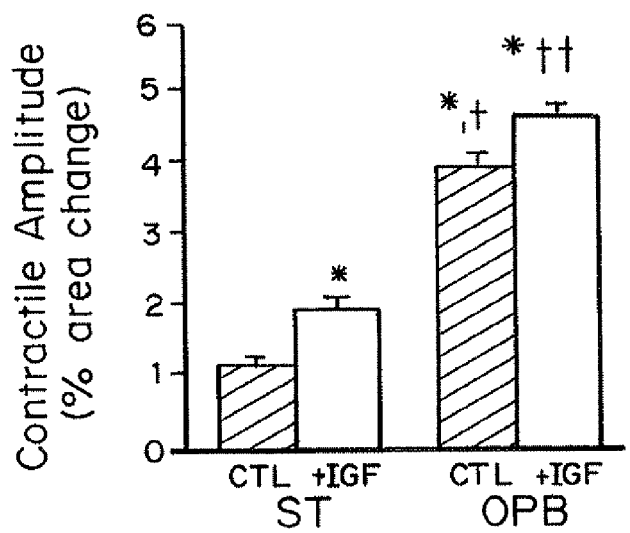
Figure 4G:
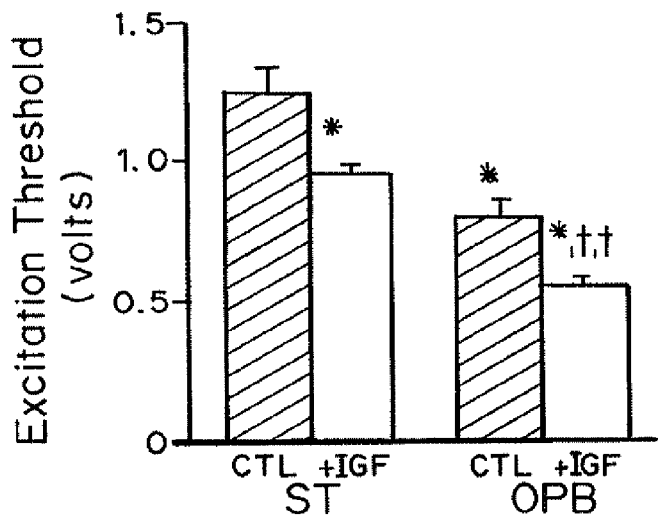

Results and Discussion:

Cell viability was significantly increased by the OPB and by IGF (FIG. 4A), and apoptosis was significantly reduced by the OPB and by IGF (FIG. 4B). Two markers of cardiomyocyte differentiation (cardiac Tn-I and connexin-43) were significantly increased by the OPB (FIG. 4 C-D); these markers were also increased by IGF but not significantly. Total protein content was significantly increased by the OPB (FIG. 4E). Contractile amplitude was significantly increased by the OPB and by IGF (FIG. 4F), and excitation threshold was significantly reduced by the OPB and by IGF (FIG. 4G). Spontaneous, synchronous contractility was readily observed in 8-day constructs cultured in the OPB (OPB CTL, OPB+IGF), but not in constructs cultured statically (ST CTL, ST+IGF). In ST CTL and ST+IGF groups, the cells appeared rounded and expressed low levels of cardiac Tn-I, whereas in the OPB CTL and OPB+IGF groups the cells were elongated and exhibited centrally positioned elongated nuclei and characteristic cross-striations as are characteristic of native heart tissue. Significant improvements in all quantified constructs properties (Table 1) in association with enhanced cell elongation, suggests that perfusion culture in the OPB enhanced cardiomyocyte viability, differentiation, contractility, and hence the regeneration of myocardial tissue. These results were published by Cheng, M. Y., Moretti, M., Engelmayr, G. C., Freed, L. E., (2007) *Circulation* 116: II-591).

TABLE 1

Individual and interactive effects of experimental parameters on cardiac construct properties.

| | Culture Vessel | | | | | | Interactive |
|---|---|---|---|---|---|---|---|
| | Static | Static | Bioreactor | Bioreactor | Individual effect of | Individual effect Of | effect of Bioreactor |
| | | Culture Medium | | | | | |
| 8-day construct property | CTL | IGF | CTL | IGF | Bioreactor | IGF | and IGF |
| TUNEL positive cells (%, a"3) | 53.8 ± 5.6 | 23.8 ± 1.9* | 14.1 ± 1.3* | 3.83 ± 0.6*† | P < 0.01 | P < 0.01 | P < 0.01 |
| MIT (OD units/construct"5) | 0.24 ± 0.005 | 0.34 ± 0.014* | 0.61 ± 0.0019*† | 0.68 ± 0.022*†‡ | P < 0.01 | P < 0.01 | NS |
| Cardiac Tropoain-1 (% of native, a"3) | 1.7 ± 1.7 | 6.4 ± 2.5 | 31 ± 4.02*† | 40 ± 6.4*† | P < 0.01 | NS | NS |
| Coaaxxin-13 (% of native, a"3) | 18 ± 6.48 | 31 ± 7.04 | 39 ± 23 | 42 ± 4.04* | P < 0.05 | NS | NS |
| Total Protein (mg/construct, a"5) | 0.79 ± 0.02 | 0.84 ± 0.04 | 1.16 ± 0.08*† | 1.29 ± 0.09*† | P < 0.01 | NS | NS |
| Contractile Amplitude (% area change, n"12) | 1.14 ± 0.05 | 1.96 ± 0.09* | 3.93 ± 0.17*† | 4.701 ± 0.12*†‡ | P < 0.01 | P < 0.01 | NS |
| Excitation Threshold (volts, a"12) | 1.26 ± 0.08 | 0.97 ± 0.02* | 0.82 ± 0.05* | 0.57 ± 0.03*†‡ | P < 0.01 | P < 0.01 | NS |
| Construct wet weight (mg, a"5) | 42.6 ± 1.6 | 43.8 ± 1.9 | 51.4 ± 4.8 | 50.6 ± 3.8 | P < 0.05 | NS | NS |
| DNA (μg/construct a"5) | 11.4 ± 1.56 | 12.7 ± 0.94 | 13.8 ± 1.32 | 14.7 ± 0.7 | NS | NS | NS |

Abbreviations: CTL = control medium; IGF = medium supplemented with insulin-like growth factor I; TUNEL = terminal deoxynucleotidyl transferase; Biotin-2-deoxyuridine 5-triphosphate nick end labeling; MTT = 3-(4,5-dimethylthiazol-2-yl)-2,5-diphenyltetraxolium bromide DNA = deoxyribonucleic acid; NS = not statistically significant. Data represent the mean ± SEM of n = 3 to 12 independent samples.
*Significantly different (p < 0.05 by Tukey test) from corresponding constructs in the static CTL group.
†Significantly different (p < 0.05 by Tukey test) from corresponding constructs in the static + IGF group.
‡Significantly different (p < 0.05 by Tukey test) from corresponding constructs in the bioreactor CTL group.

Example 3

Perfusion Culture after Seeding

Materials and Methods.

Cells harvested from neonatal rat hearts were seeded on 3D porous solid scaffolds by entrapment in one of three different hydrogels (i.e. MATRIGEL®, a self-assembling peptide gel, PURAMATRIX®, and fibrin gel) and then cultured for 8 days either statically (ST) or in the oscillatory perfused bioreactor (OPB). To provide an index of culture aerobicity, the molar ratio of lactate produced to glucose consumed (Lac/Glu ratio) was calculated, wherein values of 1.0 and 2.0 indicate purely aerobic and purely anaerobic metabolism, respectively.

Result and Discussion.

Figure 5:
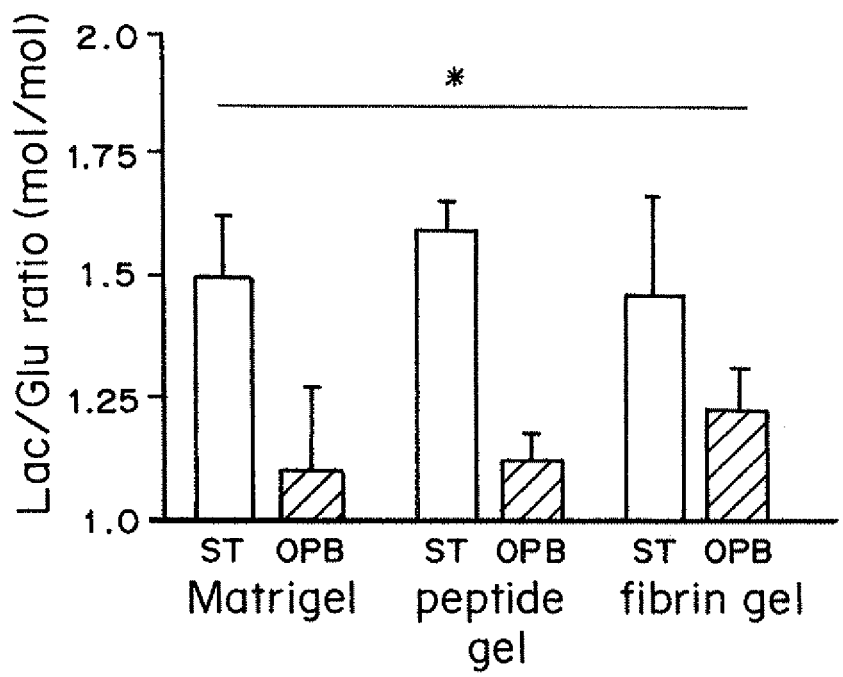
FIG. 5. is a graph of lactate/glucose ratio, an index of culture aerobicity during static (ST) or oscillating perfused bioreactor (OPB) culture of cardiomyocytes entrapped within 3D porous scaffolds using three different gels (Matrigel, self assembling peptide gel and fibrin gel), demonstrating that the bioreactor provides more aerobic culture conditions than static culture. Data are average±SD of duplicative measurements; * significant difference due to the culture method.

The Lac/Glu ratio was significantly lower for bioreactor than static cultures of cells (cardiomyocytes) entrapped within 3D porous scaffolds using three different hydrogels (FIG. 5). This result supports the use of the OPE for maintaining aerobicity during culture of large tissue constructs Example 4

Maintenance of Cell Viability prior to Transplantation

Materials and Methods:

Cells harvested from neonatal rat hearts were cultured in suspension in either the oscillating perfused bioreactor (OPB), spinner flasks (SF), or orbitally mixed flasks (MF). Aliquots of these cell suspensions were sampled at days 0, 2, 4, 6, 8 and cell viability was quantified by trypan blue exclusion.

Figure 6:
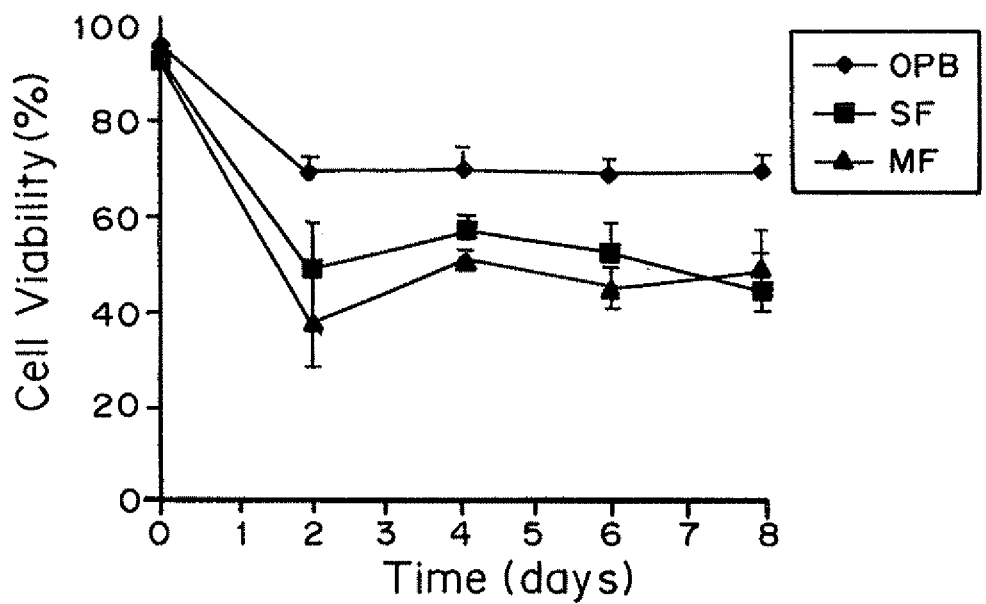
FIG. 6 is a graph demonstrating that the bioreactor promotes maintenance of cell viability, plotting percent cell viability over time for cardiomyocytes cultured in suspension in the oscillating perfused bioreactor (OPB), spinner flasks (SF), or orbitally mixed flasks (MF). Data are the average±SD of n+3 measurements.

Result and Discussion:

Cell viability was better maintained in the OPB than either the SF or MF groups, and by culture day 8, the OPB yielded approximately 50% higher cell viability than either SF or MF (FIG. 6). This result shows the use of the OPB for maintaining cell viability prior to transplantation.

We claim:

1. A bioreactor comprising
   one or more gas permeable, closed-loop chambers which can contain fluid and gases and a tissue engineering scaffold for cell or tissue culture;
   a tissue engineering scaffold or tissue engineering matrix secured directly to the wall of the closed-loop chamber or placed within a means for retaining the scaffold which is secured directly to the wall of closed-loop chamber so that fluid, cells and gases are forced through the entire thickness of the scaffold; and
   an oscillator and controller for moving the gas permeable, closed-loop chamber bidirectionally along an axis horizontal to an axis normal to the closed-loop chamber to force cells and fluid within the gas permeable, closed-loop chamber by convective flow through the secured tissue engineering scaffold.

2. The bioreactor of claim 1, wherein the gas permeable, closed-loop chamber is toroidal.

3. The bioreactor of claim 1, further comprising a plurality of gas permeable, closed-loop chambers.

4. The bioreactor of claim 1, further comprising a housing for providing controlled environmental conditions.

5. The bioreactor of claim 4, comprising means for maintaining humidity, means for regulating temperature at about 35-37° C., and means for controlling gases to about 21% oxygen and between about 5-10% $CO_2$.

6. The bioreactor of claim 4, wherein the housing oxygenates and buffers the pH of a fluid in the gas permeable, closed-loop chamber.

7. The bioreactor of claim 1, wherein the gas permeable, close-looped chamber comprises a gas-permeable polymer.

8. The bioreactor of claim 7, wherein the gas-permeable polymer is silicone rubber.

9. The bioreactor of claim 7 wherein the polymer is translucent or transparent.

10. The bioreactor of claim 1, further comprising therein cells on the scaffold or tissue engineering matrix.

11. The bioreactor of claim 10 wherein the cells are mammalian cells selected from the group consisting of cardiac cells, mesenchymal cells, fibroblasts, interstitial cells, neural cells, endothelial cells, smooth or skeletal muscle cells, myocytes, chrondocytes, adipocytes, fibromyoblasts, ectodermal cells, ductile and skin cells, hepatocytes, Islet cells, cells present in the intestine, parenchymal cells, osteoblasts, bone marrow cells, blood cells, and stem cells.

12. The bioreactor of claim 1, further comprising a hydrogel in combination with the scaffold or matrix.

13. The bioreactor of claim 1 wherein the scaffold is a hydrogel.

14. The bioreactor of claim 1 comprising cells to be cultured to form cardiac tissue, cartilage, bone, muscle or skin tissue.

15. The bioreactor of claim 1 wherein convective flow is achieved by trapping a bubble at the top of the closed-loop chamber or using a partially occlusive roller which compresses tubing at the top of the closed-loop chamber.

16. A method for culturing cells comprising
    culturing the cells in a bioreactor comprising
    one or more gas permeable, closed-loop chambers which can contain fluid and gases and a tissue engineering scaffold for cell or tissue culture;
    a tissue engineering scaffold or tissue engineering matrix secured directly to the wall of the closed-loop chamber or placed within a means for retaining the scaffold which is secured directly to the wall of the closed-loop chamber so that fluid, cells and gases are forced through the entire thickness of the scaffold; and
    an oscillator and controller for moving the gas permeable, closed-loop chamber bidirectionally along an axis horizontal to an axis normal to the closed-loop chamber to force cells and fluid within the gas permeable, closed-loop chamber by convective flow through the secured tissue engineering scaffold.

17. The method of claim 16 for producing a scaffold or tissue engineering matrix comprising
    placing a scaffold or tissue engineering matrix and culture media in the gas permeable, closed-loop chamber;
    sealing the gas permeable, closed-loop chamber;
    oscillating the gas permeable, closed-loop chamber bidirectionally along an axis horizontal to an axis normal to the closed-loop chamber to force convection of the culture media and cells through the scaffold; and
    culturing the cells in the bioreactor.

18. The method of claim 17, wherein the cells are selected from the group consisting of cardiac cells, mesenchymal cells, fibroblasts, interstitial cells, neural cells, endothelial cells, smooth or skeletal muscle cells, myocytes, chrondocytes, adipocytes, fibromyoblasts, ectodermal cells, ductile and skin cells, hepatocytes, Islet cells, cells present in the intestine, parenchymal cells, osteoblasts, bone marrow cells, blood cells, and stem cells.

19. The method of claim 16 wherein convective flow is achieved by trapping a bubble at the top of the closed-loop chamber or using a partially occlusive roller which compresses tubing at the top of the closed-loop chamber.

* * * * *